(12) United States Patent
Hassell et al.

(10) Patent No.: US 12,031,908 B2
(45) Date of Patent: Jul. 9, 2024

(54) FABRY PEROT INTERFEROMETRY FOR MEASURING CELL VIABILITY

(71) Applicant: Nirrin Technologies, Inc., Billerica, MA (US)

(72) Inventors: Bryan A. Hassell, Cambridge, MA (US); Walid A. Atia, Jamaica Plain, MA (US); David P. Marchessault, Hopkinton, MA (US)

(73) Assignee: Nirrin Technologies, Inc., Billerica, MA (US)

( * ) Notice: Subject to any disclaimer, the term of this patent is extended or adjusted under 35 U.S.C. 154(b) by 297 days.

(21) Appl. No.: 17/094,901

(22) Filed: Nov. 11, 2020

(65) Prior Publication Data

US 2021/0140881 A1 May 13, 2021

Related U.S. Application Data

(60) Provisional application No. 63/053,280, filed on Jul. 17, 2020, provisional application No. 62/933,583, filed on Nov. 11, 2019.

(51) Int. Cl.
*B01L 3/00* (2006.01)
*B01F 23/00* (2022.01)
(Continued)

(52) U.S. Cl.
CPC ............ *G01N 21/39* (2013.01); *C12M 41/32* (2013.01); *G01N 21/3577* (2013.01);
(Continued)

(58) Field of Classification Search
CPC .. G01N 21/39; G01N 21/3577; G01N 21/359; G01N 21/45; G01N 33/6854;
(Continued)

(56) References Cited

U.S. PATENT DOCUMENTS

2008/0186508 A1\* 8/2008 Kiesel .................... G01N 21/45
356/519
2011/0244588 A1\* 10/2011 Maity .................... G01N 21/45
436/164

(Continued)

OTHER PUBLICATIONS

International Preliminary Report on Patentability, mailed on May 27, 2022, from International Application No. PCT/US2020/059919, filed on Nov. 11, 2020. 8 pages.

(Continued)

*Primary Examiner* — Jennifer Wecker
*Assistant Examiner* — Oyeleye Alexander Alabi
(74) *Attorney, Agent, or Firm* — HoustonHogle LLP

(57) ABSTRACT

A method for studying cell viability and protein aggregation involves establishing a Fabry Perot etalon signal within an optical spectroscopic feature, e.g., in the near infrared region. Protein aggregation and cell viability can be reflected by changes observed in the magnitude of the Fourier Transform peaks observed in the frequency or space domain associated with the contrast of the etalon. In short, the presence of viable cells and protein aggregates can degrade the etalon contrast of an etalon window. In some cases, the concentration of cells and monomeric protein can be measured as well.

19 Claims, 17 Drawing Sheets

(51) Int. Cl.
| | |
|---|---|
| *B01F 23/41* | (2022.01) |
| *B01F 101/23* | (2022.01) |
| *B23Q 17/24* | (2006.01) |
| *C12M 1/34* | (2006.01) |
| *C12Q 1/18* | (2006.01) |
| *G01N 21/3577* | (2014.01) |
| *G01N 21/359* | (2014.01) |
| *G01N 21/39* | (2006.01) |
| *G01N 21/45* | (2006.01) |
| *G01N 21/64* | (2006.01) |
| *G01N 33/50* | (2006.01) |
| *G01N 33/68* | (2006.01) |

(52) U.S. Cl.
CPC ........... *G01N 21/359* (2013.01); *G01N 21/45* (2013.01); *G01N 33/6854* (2013.01); *G01N 2201/06113* (2013.01)

(58) Field of Classification Search
CPC ... G01N 2201/06113; G01N 2021/399; G01N 21/8507; G01N 2021/451; G01N 21/31; C12M 41/32; G01J 3/26
See application file for complete search history.

(56) References Cited

U.S. PATENT DOCUMENTS

| | | | | |
|---|---|---|---|---|
| 2014/0177932 | A1* | 6/2014 | Milne | G01N 21/31 |
| | | | | 382/128 |
| 2019/0272894 | A1 | 9/2019 | Wasalathanthri et al. | |
| 2019/0358632 | A1 | 11/2019 | Hassell et al. | |
| 2021/0062133 | A1 | 3/2021 | Hassell et al. | |
| 2021/0088433 | A1 | 3/2021 | Hassell et al. | |
| 2021/0371785 | A1 | 12/2021 | Hassell et al. | |

OTHER PUBLICATIONS

Park, J., "Monitoring change in refractive index of cytosol of animal cells on affinity surface under osmotic stimulus for label-free measurement of viability," Biosensor and Bioelectronics, 64: 241-246 (2015).
Choi, W., et al., "Tomographic phase microscopy," Nature Methods, 4(9): 717-719 (2007).
Cervera, A. E., et al., "Application of near-infrared spectroscopy for monitoring and control of cell culture and fermentation," Biotechnol. Prog. 25(6): 1561-1581 (2009).
Davies, A.M.C., "An Introduction to Near Infrared (NIR) Spectroscopy", http://www.impublications.com/content/introduction-near-infrared-nir-spectroscopy, (2020).
Mazzer, A.R., et al., "Protein A Chromatography Increases Monoclonal Antibody Aggregation Rate During Subsequent low pH Virus Inactivation Hold," J. Chromatogr. A, 1415: 83-90 (2015).
Molodenskiy, D., et al., "Thermally Induced Conformational Changes and Protein-Protein Interactions of Bovine Serum Albumin in Aqueous Solution under Different pH and Ionic Strengths as Revealed by SAXS Measurements," Phys. Chem. Chem. Phys., 19(26): 17143-17155 (2017).
Roberts, C.J., "Protein Aggregation and Its Impact on Product Quality," Curr. Opin. Biotechnol., 211-217: (2014).
Roggo, Y, et al., "A review of near infrared spectroscopy and chemometrics in pharmaceutical technologies," Journal of Pharmaceutical and Biomedical Analysis, 44(3): 683-700 (2007).
Wang, C., et al., "Holographic Characterization of Protein Aggregates," J. Pharm. Sci., 105(3): 1074-1085 (2016).
Ingraham, P., et al., "High-Contrast Imaging Performance of a Tunable Filter for Space-Based Applications. II. Detection and Characterization Capabilities," Astronomical Society of the Pacific, 124: 454-468 (2012).
Liu, B., "Optimal beam forming for laser beam propagation through random media," Michigan Technological University, 1-131 (2006).
Knaysi, G., "A Microscopic Method of Distinguishing Dead from Living Bacterial Cells," New York State College of Agriculture, 1-14 (1934).
Anonymous, "Quantitative Phase Imaging," https://phiab.com/holomonitor/quantitative-phase-imaging/, 1-6 (2017).
Anonymous, "Fabry-Perot Interferometer," Wikipedia 1-17 (accessed 2021).
Paschotta, R., "Tilt Tuning of Etalons," RP Photonics Consulting GmbH, 1-5 (2009).
Anonymous, "Trypan Blue Exclusion," ThermoFisher Scientific, 1 (accessed 2021).
Anonymous, "LIVE/DEAD Cell Viability Assays," ThermoFisher Scientific, 1-4 (accessed 2021).
International Search Report and Written Opinion of the International Searching Authority, mailed on Feb. 9, 2021, from International Application No. PCT/US2020/059919, filed on Nov. 11, 2020. 13 pages.
O'Connor, C.M., 4.6 Exercise 3—Estimating Cell Densities with a Spectrophotometer, LibreTexts, 1 (1979).
Anonymous, "Lecture 18: Multiple Beam Interference Introduction to Fabry-Perot Spectroscopy," 1-14 (2012).

* cited by examiner

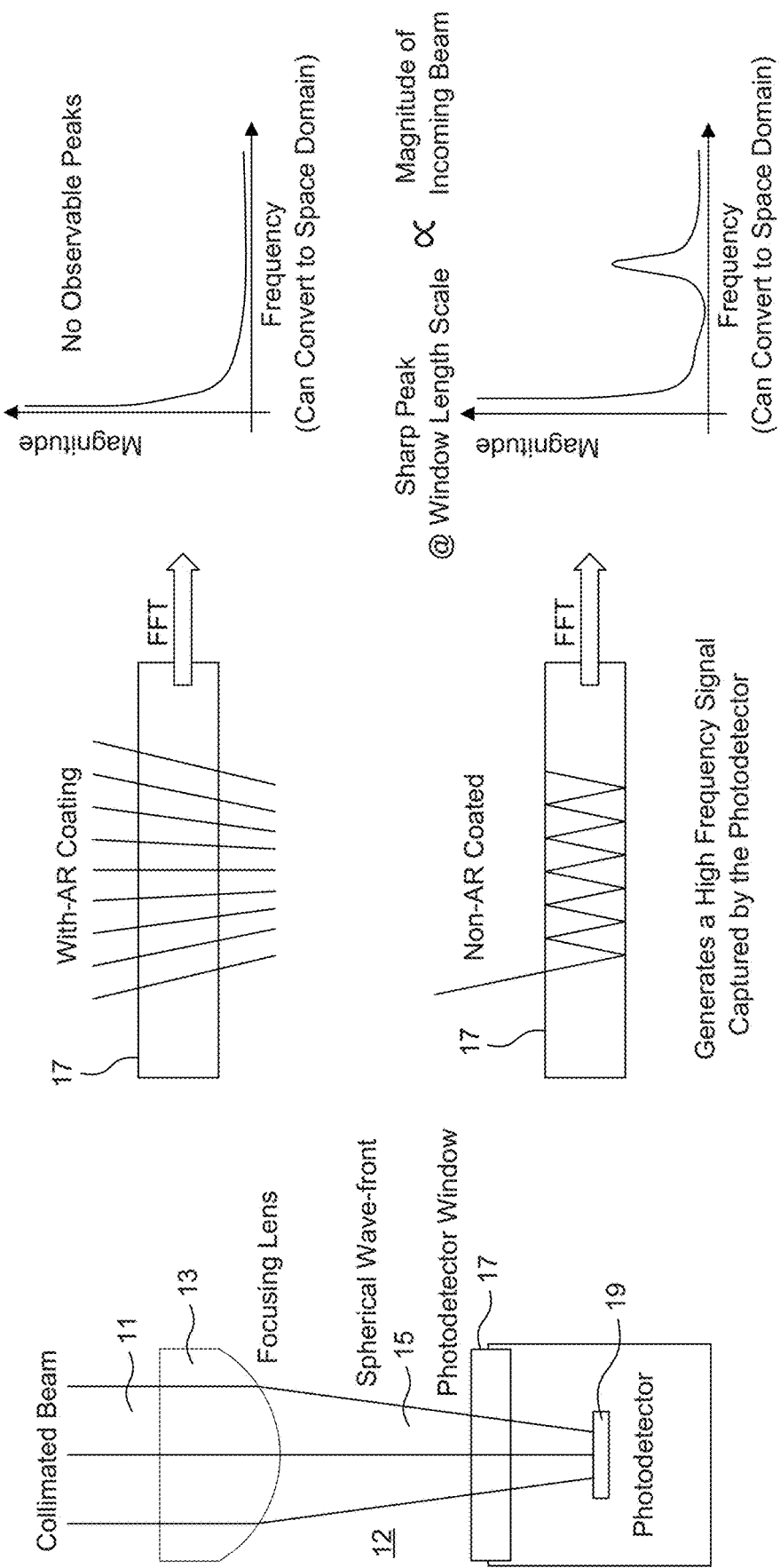

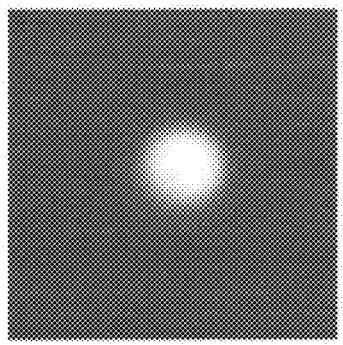 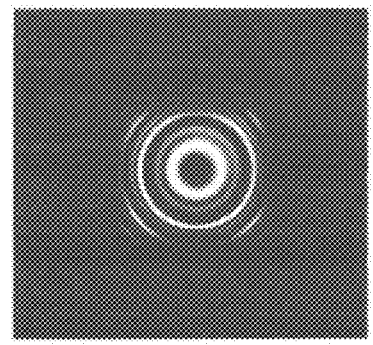
FIG. 2A  FIG. 2B
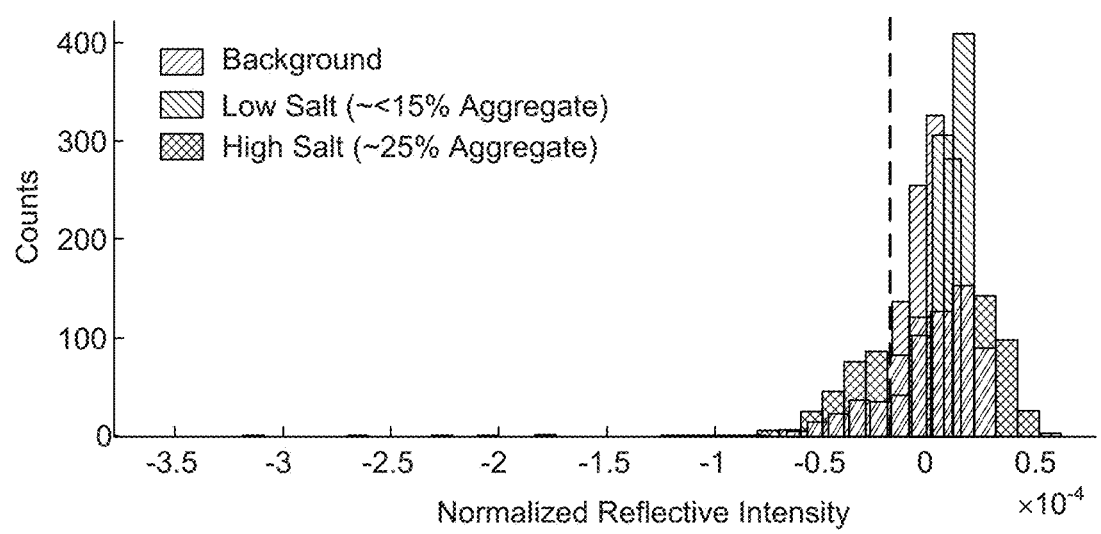
FIG. 12

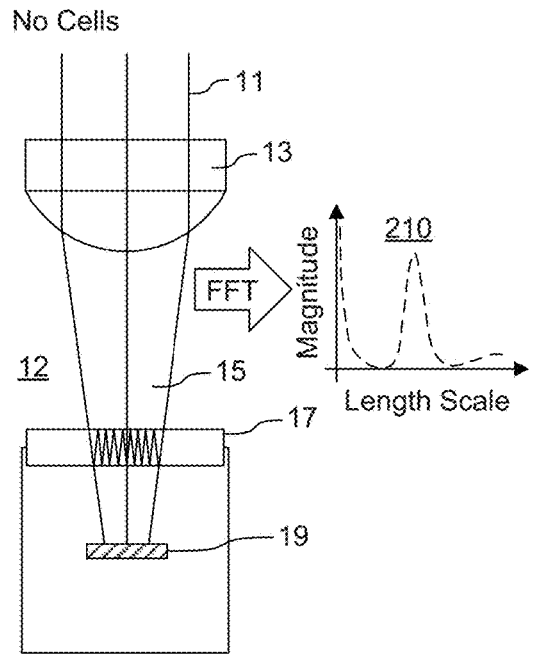
FIG. 3A
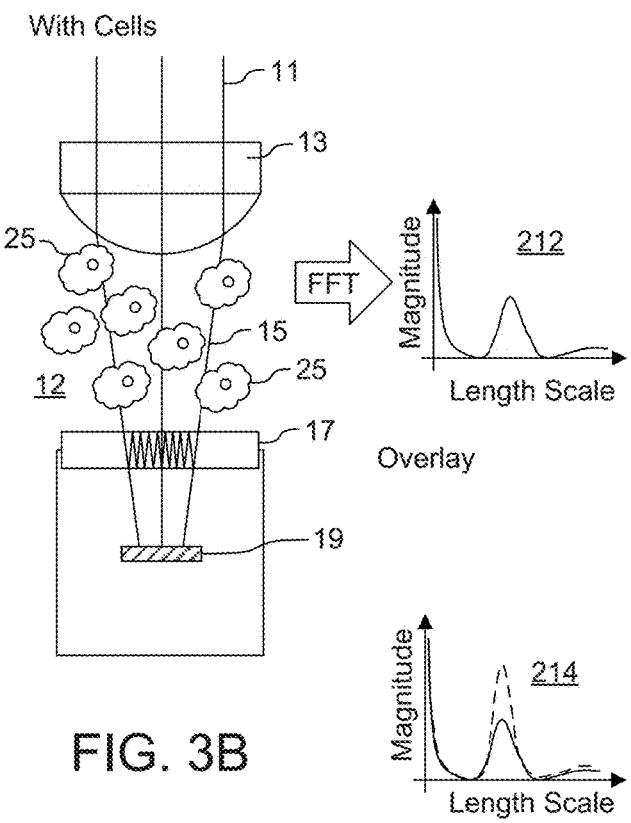
FIG. 3B
FIG. 3C
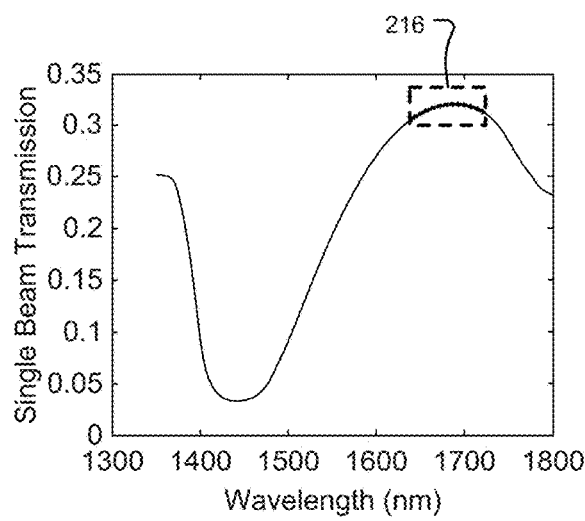
FIG. 4A
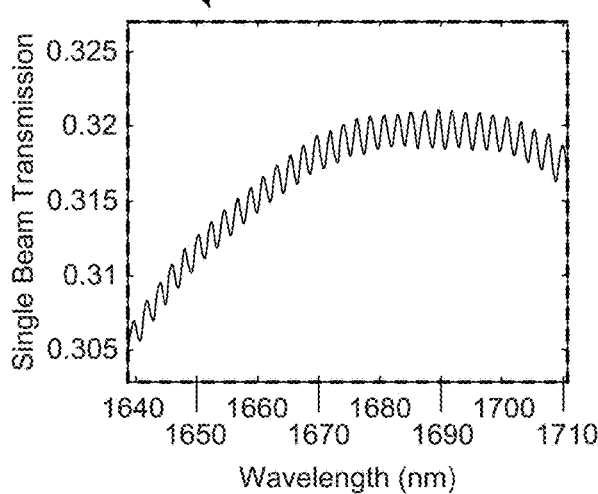
FIG. 4B

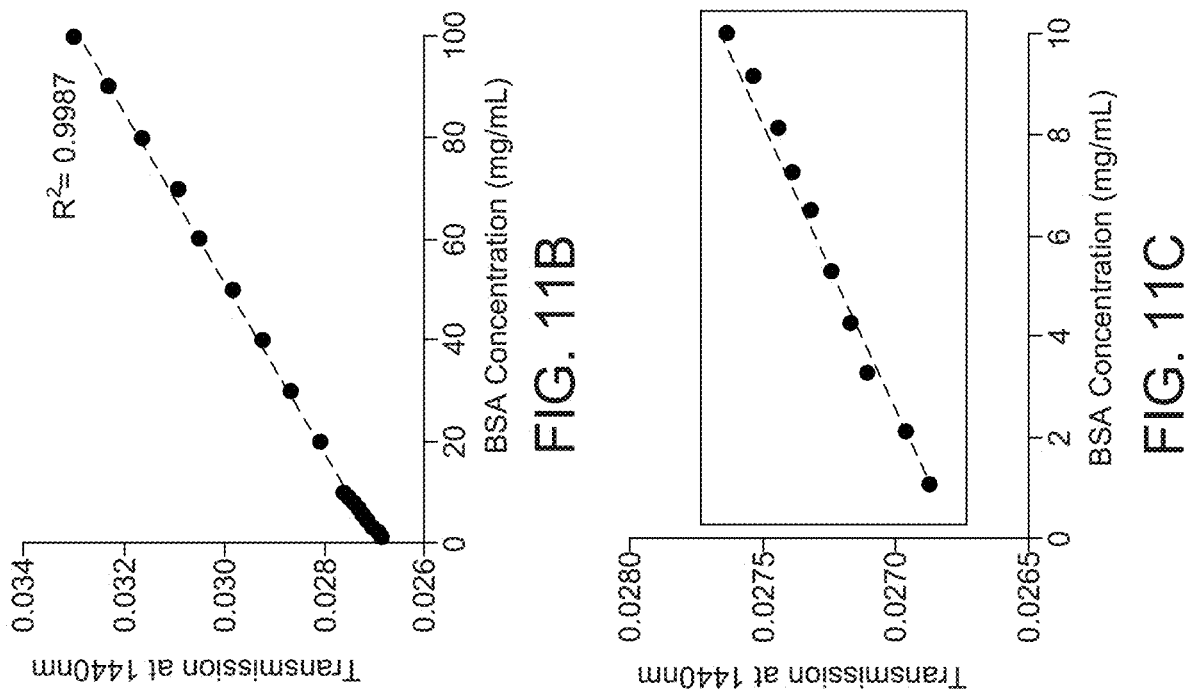
FIG. 11B
FIG. 11C
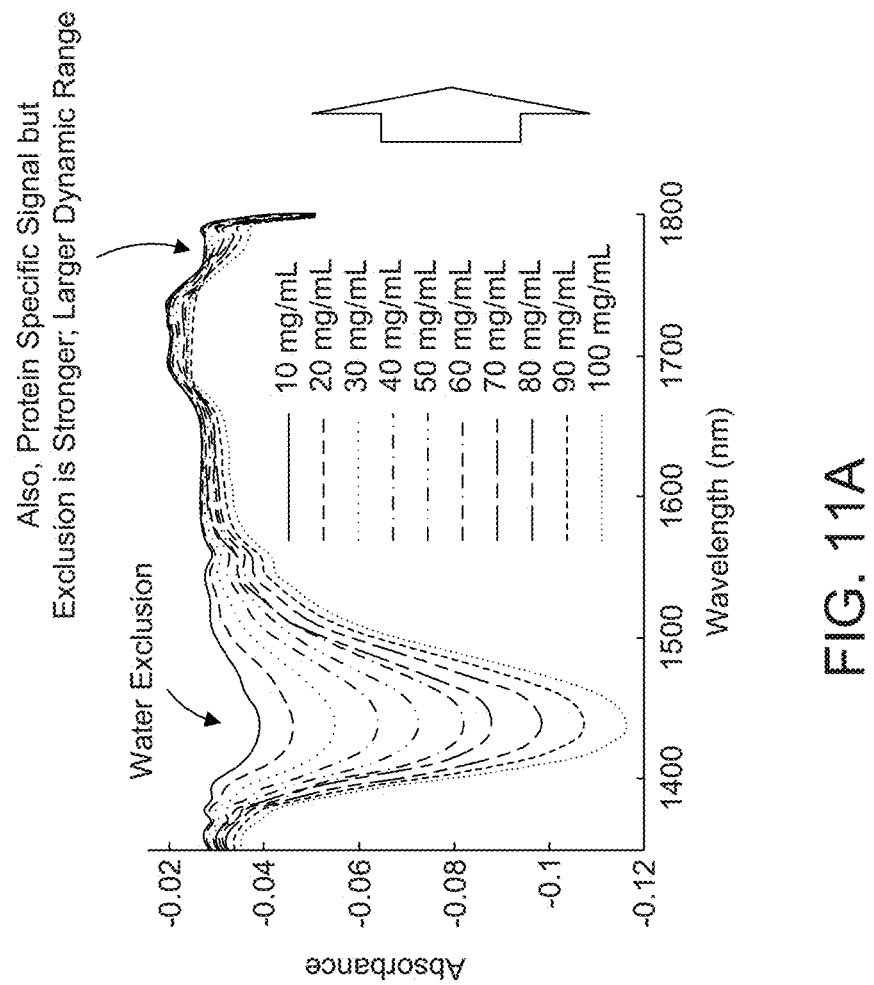
FIG. 11A

FABRY PEROT INTERFEROMETRY FOR MEASURING CELL VIABILITY

RELATED APPLICATIONS

This application claims the benefit under 35 USC 119(e) of U.S. Provisional Application No. 62/933,583, filed on Nov. 11, 2019 and U.S. Provisional Application No. 63/053,280, filed on Jul. 17, 2020, which both are incorporated herein by reference in their entirety.

BACKGROUND OF THE INVENTION

Many processes in the chemical, biochemical, pharmaceutical, food, beverage and in other industries require some type of monitoring. Sensors have been developed and are available to measure pH, dissolved oxygen (DO), temperature or pressure in-situ and in real-time. Common techniques for detecting chemical constituents include high performance liquid chromatography (HPLC), gas chromatography-mass spectroscopy (GCMS), or enzyme- and reagent-based electrochemical methods.

Various optical spectroscopy approaches are also available to assess components, also referred to as analytes, in a sample. Among these, probably the most common is absorption spectroscopy. Incident light excites electrons of the analyte from a low energy ground state into a high energy, excited state, and the energy can be absorbed by both non-bonding n-electrons and π-electrons within a molecular orbital. Absorption spectroscopy can be performed in the ultraviolet, visible, and/or infrared region, with analytes of varying material phases and composition being interrogated by specific wavelengths or wavelength bands of light. The resulting transmitted light is then used to resolve the absorbed spectra, to determine the analyte's or sample's composition, temperature, pH and/or other intrinsic properties for applications ranging from medical diagnostics, pharmaceutical development, food and beverage quality control, to list a few.

Another option is Raman spectroscopy, which works by the detection of inelastic scattering of typically monochromatic light from a laser.

Many of the processes being monitored also involve growing and/or maintaining cells. In such situations, the viability of the cells cannot be overemphasized.

In a similar vein, proteins, such as, for instance, monoclonal antibodies, are becoming increasingly important in medicine and thus constitute a significant sector of the biopharmaceutical market. The production of proteins, especially in the context of commercial scale manufacturing, presents various challenges, however. Many relate to protein degradation.

It is known, for example, that protein aggregates can cause problems (immunogenicity), if administered to patients. As a result, many existing production processes incorporate filtration-based measures to reduce aggregate amounts to an acceptable level.

Monitoring and/or quantifying aggregates can be very time consuming and, in many cases, not very accurate. In *Holographic Characterization of Protein Aggregates*, J. Pharm. Sci., 2016 March; 105(3): 1074-1085, PMC6292201, published online 2016 Feb. 2, C. Wang et al. describe a method based on holographic video microscopy for detecting, counting and characterizing individual colloidal particles in suspension. The method is reported to distinguish protein aggregates from contaminants such as silicone droplets (based on differences in their optical properties) and to rapidly build up population statistics on subvisible protein aggregates in their natural state, without requiring dilution or special solvent conditions.

SUMMARY OF THE INVENTION

Some of the existing techniques for measuring cell densities (total and/or viable) utilize an exclusion dye, which can be fluorescent. Also known are spectrophotometric methods.

Typical approaches can be destructive as they rely on removing and analyzing samples off-line. This may be particularly problematic when measuring cell densities.

In addition, protocols followed in analyzing cell cultures often require expensive consumables and/or a long time to complete. In many cases, the equipment needed to perform these analyses is expensive, involving calibrations, and trained operators. Procedures may be time- and labor-intensive, problems that are often mitigated by decreasing the sampling frequency of a given process, thus reducing the data points. In many instances, samples are run in batches, after the process has been completed, yielding little or no feedback for adjusting conditions on an ongoing basis. Drawbacks such as these can persist even with automated sampling operations.

A need exists for robust, hands-free, non-destructive, real time techniques for identifying and/or quantifying cell densities and, possibly, other constituents in an ongoing process. For procedures in which cells are used to produce antibodies or procedures in which cells themselves are the product, such as those involved in cell therapy procedures, non-destructive, real time techniques for measuring cell viability are also highly desirable. Also desirable are approaches for monitoring cell viability in situ, without the need to withdraw samples from the culture vessel being employed, often a bioreactor.

In addition, with the increased importance of preparing pharmaceutical grade monoclonal antibodies or other proteins, a need also continues to exist for approaches that can detect protein aggregates in real time. Also needed are robust, hands-free, non-destructive techniques for quantifying these aggregates. Methods for in situ ongoing measurements that can be conducted under flow conditions (during downstream protein bioprocessing, for example), without a need to withdraw and analyze samples off-line, are desirable as well.

In general, the invention relates to monitoring and assessing structures (cells, proteins and so forth) in samples. In one case, this entails measuring or monitoring cell density and/or viability in ways that address at least some of the problems described above. It can also relate to approaches for measuring protein aggregates. Optionally, the amounts of the protein (in its monomeric or unaggregated form) can be measured as well. In some embodiments, both protein concentrations and aggregation levels are measured simultaneously. In turn, this information can be used to determine, e.g., statistically, percent aggregation for a specific process.

In many of its aspects, the invention relies on an optical arrangement in which a Fabry Perot etalon is established, possibly in a photodetector window that does not utilize an antireflective coating or that employs a reflective coating. It was discovered that passing a spherical wave-front through a cell culture containing viable cells produced a signal (e.g., peak) having a magnitude as a function of wavelength (whether in a frequency or space domain) that decreased with respect to the magnitude of a signal obtained in the absence of viable cells. Furthermore, the magnitude of the signal was found to change as the number or ratio of viable cells changed. In many embodiments, peaks generated from the etalon are superimposed onto an optical transmission spectrum, in the near infrared region, for example. Some implementations utilize etalons established in stand-alone windows, microscope slides, other optical components or substrate. In one example, the etalon is established in a volumetric sample detection region and/or that at least partially overlaps that region.

Approaches described herein also can be implemented on a fluid that, in some embodiments, is in a state of flow. In one illustration, protein aggregates (soluble protein aggregates, for instance), optionally in conjunction with monomeric protein levels, are monitored at a suitable point during downstream bioprocessing (processing that typically occurs after the separation of the protein-containing fluid from the protein-producing cells). In one implementation, measuring protein aggregation is conducted post protein A column.

Some of the arrangements and/or techniques described herein are configured to probe a bioreactor in situ. Monitoring not only viable cells and proteins, but also other analytes present in the medium also is possible.

Aspects of the invention can be practiced in bioprocesses such as those used in the production of monoclonal antibodies or in cell therapy applications, where the cells themselves represent the product to be administered to a subject. Embodiments described herein also can find applications in detecting bioburden in various fields (e.g., various processes in biotechnology or the pharmaceutical industry, wastewater treatment, food and beverage, and so forth).

The advantages of measuring cell viability in situ cannot be overemphasized. Techniques described herein can provide on-line, real time measurements, obtained in a non-destructive manner. Whereas many existing approaches rely on removing and/or circulating cells in loops external to the process vessel, typically through a pumping system, some of the embodiments described herein can reduce, minimize and often eliminate the exposure of cells to conditions external to the bioreactor. In addition, cells are prevented from being drawn into the pumping system.

Aspects of the invention also explore using the reflective strength of a Fabry Perot etalon to capture changes, often subtle, in refractive index such as due to protein aggregation. Some of the techniques employed rely on absorption measurements, e.g., in the near infrared (NIR) region of the electromagnetic spectrum, to determine protein concentrations, and a frequency and etalon measurement to determine protein aggregation. Specific implementations employ a beam splitter to obtain both an absorption measurement and the interferometric measurement where one or more etalons are in the beam path after and also possibly optically before the sample. It may also be possible to establish the etalon gap within or overlapping the sample space itself. In one example the absorption measurement is used to provide information on protein concentration (and other concentrations, salt concentrations, for instance); that information can then be used to determine if the etalon signal of the interferometric measurement will be changing or become offset in real-time.

The invention can find applications in optimizing cell growth, in support of product purification, quality control, product recovery or other stages in the manufacture of proteins or other areas. Techniques described herein can provide real-time cell viability data, protein and aggregation concentrations and can render the aggregate measurement more accurate. Providing valuable information about structures of interest, protein aggregation, for instance, embodiments described herein can be conducted online, e.g., during an ongoing flow process. Measurements can be obtained rapidly, in situ and in real time, using non-destructive approaches, without the need to withdraw aliquots or divert a portion of the flow.

In practice, a real-time method for quantifying aggregates can be used to "chop the peak" meaning that, as the real target (the monomer protein) is eluting, it is possible to detect when non-ideal aggregates are coming off the column and divert the flow, so that the collected fraction is a more purified resulting product.

In some cases, techniques described herein can further be used to obtain additional information regarding non-cell analytes, such as lactate, glucose, and so forth. Thus, practicing embodiments of the invention can provide an overall picture, monitoring multiple constituents present in the cell culture or other production processes.

Some implementations use a device that can be or can include disposable components. Typically, the device can be inserted and/or maintained in a bioreactor or other vessel or transfer line and incorporates elements for viewing as well as elements needed to analyze the contents, e.g., in the NIR region of the electromagnetic spectrum. The analysis can be conducted in real time, in a rapid and nondestructive manner.

In general, according to one aspect, the invention features a system for analyzing for structures in a solution. The system comprises a light source for illuminating the solution across a spectral band, a detector for detecting light from the light source after interaction with the solution and an etalon, and a controller that analyses a response of the detector to resolve contrast information of the etalon to assess the structures in the solution.

In embodiments, the structures are cells and the controller might assess a viability of the cells and/or a number of cells and/or density of the cytoplasm of the cells and/or a density of the cells in their solution.

In some cases, the structures are proteins and the controller might assess aggregation of the proteins, optionally in conjunction with assessing non-aggregated proteins.

In some cases, the solution is withdrawn from a vessel for analysis; in other cases, solution is analyzed while in a bioreactor.

In some embodiments, the controller resolves contrast information of two etalons.

Also, light from the light source is split to additionally perform absorption spectroscopic analysis of the solution.

In some cases, the detector detects light in a transmission arrangement, but in other cases, the detector detects light in a transflection arrangement.

In general, according to another aspect, the invention features a method for analyzing structures in a solution. The method comprises illuminating the solution across a spectral band, detecting light from the light source after interaction with the solution and an etalon and analyzing a response of the detector to resolve contrast information of the etalon to assess the structures in the solution.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1A is a schematic cross-sectional diagram of an optical arrangement used to measure structures such as viable cells;

FIG. 1B shows the effects obtained with a photodetector window in the presence (top) or absence (bottom) of an antireflective-coating;

FIG. 1C compares plots (in a frequency domain) after a Fast Fourier Transform (FFT) obtained for a window provided with an antireflective coating (top) and for a non-antireflective coated window (bottom);

FIGS. 2A and 2B, show, respectively, a Fabry Perot pattern obtained with an antireflective window and one obtained with a non-antireflective window in the frequency domain;

FIG. 3A presents an inset FFT spectral plot obtained with a photodetector window without an antireflective coating and a cell culture devoid of viable cells, shown in schematic cross-section;

FIG. 3B presents an inset FFT spectral plot obtained with a photodetector window without an antireflective coating and a cell culture containing viable cells, shown in schematic cross-section;

FIG. 3C presents an overlay of the inset plots of FIGS. 3A and 3B;

FIG. 4A is a single beam transmission scan, using an in situ probe of a culture medium containing Chinese Hamster Ovary cells;

FIG. 4B displays the high frequency signal generated by the etalon and submerged in the transmission scan of FIG. 4A;

FIG. 11A is a series of plots illustrating the "water exclusion" absorbance at various protein concentrations;

FIGS. 11B and 11C show the transmission at 1440 nm as a function of protein concentration;

FIG. 12 is a histogram based on multiple (1000) scans of: (i) a background solution containing no protein, either in monomeric or aggregated form; (ii) a first solution (<15% dimer); and (iii) a second solution (~25% dimer/trimer species);

FIGS. 16A and 16B are plots showing the separate signals perceived by the detector when using two etalon windows having different thicknesses in which FIG. 16A is a plot of intensity as a function of wavelength in nanometers and FIG. 16B is Fourier transform of the signal plotted in FIG. 16A;

DETAILED DESCRIPTION OF THE PREFERRED EMBODIMENTS

Figure 5A:
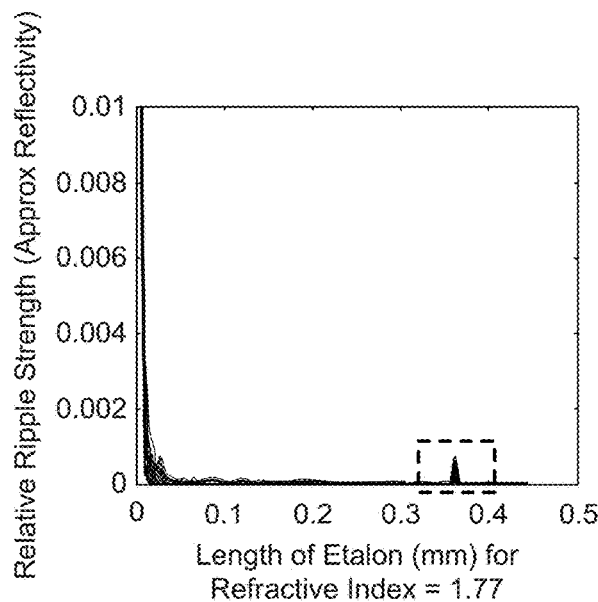
FIG. 5A shows a peak that, when FFT was converted to a space domain, occurred at 0.36 mm.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In some of its aspects, the invention relates to measuring structures such as cells, including, e.g., their densities, such as the density of their cytoplasm and/or the density of the cells and/or viability, within a medium typically a liquid-containing cell culture. In many implementations, the cells are in an aqueous medium. In other cases, the structures are proteins and protein aggregates.

Any type of cells can be detected or monitored. Examples include but are not limited to mammalian, bacterial, fungal, and many others.

The life cycle of cells is generally marked by various changes. For instance, before autolysis (i.e., the destruction of cells or tissues by their own enzymes, such as enzymes released by lysosomes) cells will typically stain a deep red. As autolysis progresses, the staining becomes gradually fainter, probably due to losses in stainable material, and the cells appear disorganized. In addition, cells undergoing autolysis have an index of refraction that approaches the index of refraction of the aqueous cell culture, possible due to a loss in cell density (the lowering of the density of the cells' cytoplasm) and/or other mechanisms. In contrast, live cells have an index of refraction that is different from that of the aqueous culture medium, resulting in a turbid environment.

If directed through the cell culture medium, a phase front of light becomes distorted by the turbidity caused by live (viable) cells. Moreover, the distortion increases as the viable cell density increases. In turn, distorted wavefronts of the beam result in a reduction in interference contrast for an etalon forming a window into the cell culture medium.

Specific embodiments of the invention relate to an integrated aberrated phase front measurement system in which a Fabry Perot contrast measurement is directly proportional to the aberrations (i.e. the number of live cells and/or the refractive index of those cells that are causing refractive index changes across the beam's phase front).

As known in the art, a Fabry Perot interferometer (FPI) or etalon is an optical cavity made from two parallel reflecting surfaces such as thin mirrors or surfaces of a substrate having a different refractive index relative to the surrounding media. When the distance between the two mirrors or surfaces is fixed, the FPI is sometimes referred to as an "etalon". Optical waves can pass through the optical cavity only when they are in resonance with it.

In the arrangement of FIG. 1A, for example, a collimated light beam 11 is focused by lens 13 to generate a curved or possibly spherical wave-front 15, which passes through a volumetric sample detection region 12 to the window 17 of a photodetector 19.

It is possible to coat one or more of the optical components with an antireflective (AR) coating, allowing light to pass through. Providing lens 13 with an AR coating, for instance, allows light to pass through and focus without some of it being reflected. Examples of suitable AR coatings include but are not limited to thin film dielectric coatings.

In contrast, some of the embodiments described herein employ internal reflections that are established in an optical element, often a window, in the absence of an AR coating or by using a reflective rather than an antireflective coating.

The effects of the presence or absence of an AR coating on window 17, for example, can be illustrated with reference to FIGS. 1B and 1C. As seen in the top diagram of FIG. 1B, if an AR coating were to be applied to this window, the spherical wave-front propagates through the window without generating any reflections or at least with a reflectance of less than about 0.2%. The output from detector 19, processed by Fast Fourier Transform (FFT), a technique based on an algorithm that, as known in the art, computes the discrete Fourier transform (DFT) of a sequence, or its inverse (IDFT), is shown as a magnitude versus frequency plot in the top section of FIG. 1C. It does not reveal an observable peak.

However, if window 17 is free of the AR coating (or provided with a reflective coating), spherical wave-front 15 gets "trapped" inside the window (bottom diagram of FIG. 1B) and the magnitude versus frequency plot (obtained by FFT), shown in the bottom section of FIG. 1C, displays a distinct (sharp) peak associated with the frequencies that can form a standing wave in the thickness of the window 17. While the two (i.e., top and bottom) plots in FIG. 1C are presented in the frequency domain, FFT can be used to convert the DFT in the frequency domain to a space domain. Such a conversion was found to produce a distinct (sharp) peak which corresponds exactly to the thickness of the detector window 17. In one example, window 17 is a sapphire window having a specified thickness of 0.35 mm and an index of refraction n of 1.77 (at NIR wavelengths).

FIGS. 2A and 2B illustrate, respectively, the pattern that would be captured by a detector 19 having an antireflective window 17 and by a detector 19 in which window 17 is free of the AR coating. Note, that the detector does not typically have spatial resolution, so the particular pattern would not be detected.

Thus, in many implementations, while lens 13 (FIG. 1A) has an AR coating, window 17 is not AR coated.

Differences observed in the absence or presence of live cells in an arrangement such as that of FIG. 1A (using a non-AR coated window) are represented schematically in FIGS. 3A and 3B. While in FIG. 3A the spherical wave-front does not encounter any deflections and simply passes through the volumetric sample detection region 12, live cells 25, having an index of refraction that is different from that of the culture medium, cause some of the light to become scattered or refracted in the volumetric sample detection region 12, reducing the contrast of the etalon window 17 and thus the signal obtained by the FFT. This difference is shown in the overlay spectrum 214 of FIG. 3C. In more detail, the FFT conversion to a space domain reveals a peak that is smaller in the presence of viable cells (see inset plot 212 of FIG. 3B) when compared to the peak observed in the absence of cells (see inset plot 210 of FIG. 3A). In short, the scattering produced by the viable cells is exhibited in a lowering of the contrast of the window etalon 17.

In practice, live cells in the culture medium are expected to change the FFT signal relative to a matched culture medium that is free of live cells. In addition, the magnitude of the peak observed with respect to the length scale will reflect changes in cell viability. For example, a peak such as that shown in plot 212 of FIG. 3B will increase as some cells undergo autolysis, since those cells are expected to approach the index of refraction of the culture medium and fewer cells with lower scattering will be encountered by the spherical wave-front.

In some arrangements, the period of the FP etalon is much higher than spectral features of the absorption spectroscopy that may be observed, allowing simultaneous measurements of peaks generated by the etalon described above, in conjunction with optical absorption spectrometry, without deleterious effects. In this respect, one factor to be considered is the thickness of the window employed. A very thin window 17, for example, might pose problems if the absorption spectral features are comparable to the spectral features of the Fabry Perot etalon. Thicknesses for the etalon may vary. As already noted, in the case of a sapphire window, the etalon can have a thickness of 0.35 mm. In most instances, the thickness of the window/etalon is greater than 0.20 mm. In another situation, an etalon established in a probe had a period completely overlapping the glucose signal (e.g., 20 nanometers (nm)). Some signals observed could be wider or narrower than others, depending on the liquid, the analyte, wavelength range and the specific type of spectrometer employed.

To resolve the period of the etalon, techniques described herein may also benefit from a spectroscopic measurement of sufficient resolution. A broadband source and a spectrometer detector of high resolution is one option. Another option is a tunable laser. While a large linewidth may turn out to be inadequate for the measurements proposed here, a tunable laser having a resolution or linewidth or a spectrometer detector resolution of less than 1 nanometer (nm) and preferable less than 0.1 nm was found suitable in resolving the etalon. An example of such a laser is available from Axsun Technologies, Inc., under the IntegraSpec XL™. In most cases, the spectral resolution of the spectroscopic measurement is at least twice the spectral features of the etalon.

In many embodiments of the invention, a high frequency signal generated in an etalon such as described above is superimposed onto a single beam transmission signal, obtained, for instance, in the near infrared (NIR) region of the electromagnetic spectrum, namely the region from 780 nanometer (nm) to 2500 nm.

Probing molecular overtone and combination vibrations, NIR spectroscopy presents a non-invasive, non-destructive investigative approach, typically involving fast scan times. An overview of NIR spectroscopy can be found, for example, in an article by A. M. C. Davies in "An Introduction to Near Infrared (NIR) Spectroscopy", http://www.impublications.com/content/introduction-near-infrared-nir-spectroscopy. See also, Cervera, A. E., Petersen, N., Lantz, A. E., Larsen, A. & Gernaey, K. V. Application of near-infrared spectroscopy for monitoring and control of cell culture and fermentation, Biotechnol. Prog. 25, 1561-1581 (2009); and Roggo Y, et al., "A review of near infrared spectroscopy and chemometrics in pharmaceutical technologies", Journal of Pharmaceutical and Biomedical Analysis, Volume 44, Issue 3, 2007. A discussion of NIR as applied to microfluidic and other systems is provided in U.S. patent application Ser. No. 16/419,690, to Hassell et al., filed on May 22, 2019, hereinafter "Hassell I" and incorporated herein in its entirety by this reference. Short-wave infrared (between 1,100 and 3,000 nanometers) or radiation in other regions of the electromagnetic spectrum also can be employed.

As an illustration, shown in FIG. 4A is a single beam transmission spectrum of Chinese Hamster Ovary (CHO) cells cultured in a bioreactor. A tunable laser was spectrally scanned over a wavelength range of 1350 nm to 1800 nm, providing the basic absorption spectra for the region. As shown in FIG. 4B, a high frequency FP etalon signal is shown for a window 216 within the greater single beam transmission signal. This high frequency signal was found to be present throughout the growth of cells in the culture medium.

The single scan rate was about 0.1 seconds and the plots provided are averages of about 20 scans. In some situations, the etalon can "wash-out", for instance in cases in which the averaging, is based on specific numerical de-resolve methods. Typically, however, differences of averaging reflect changes in the reactor. Structures (e.g., cells, etc.) are far from static, but subject to motion. While a 0.1 sec interval can generate a nice clean scan, averaging 20 such scans or increasing the time allowed to a single scan (to 2 seconds, for example) can result in bubbles or some other random artifacts. In spite of these considerations, it was found that the etalon remained surprisingly stable. In practice, it may be useful to take multiple single scans, study them and select those that appear consistent and stable (without bubbles or artifacts) for the averaging step.

Figure 5B:
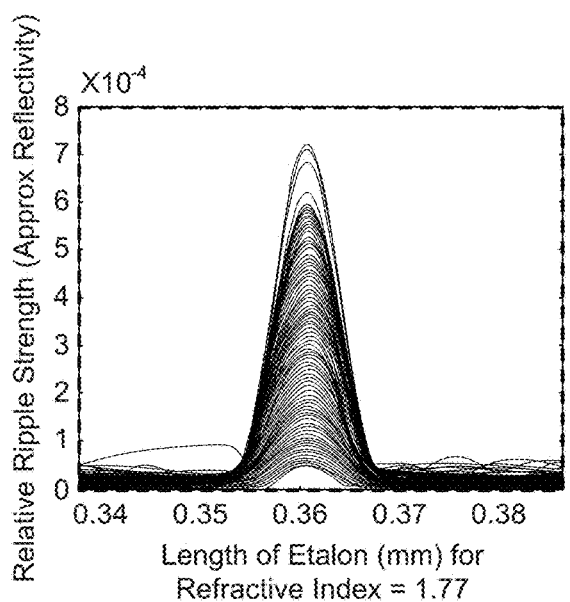
FIG. 5B is a series of plots reflecting changes in the peak magnitude of FIG. 5A measurements taken at various times during the experiment.
Figure 6:
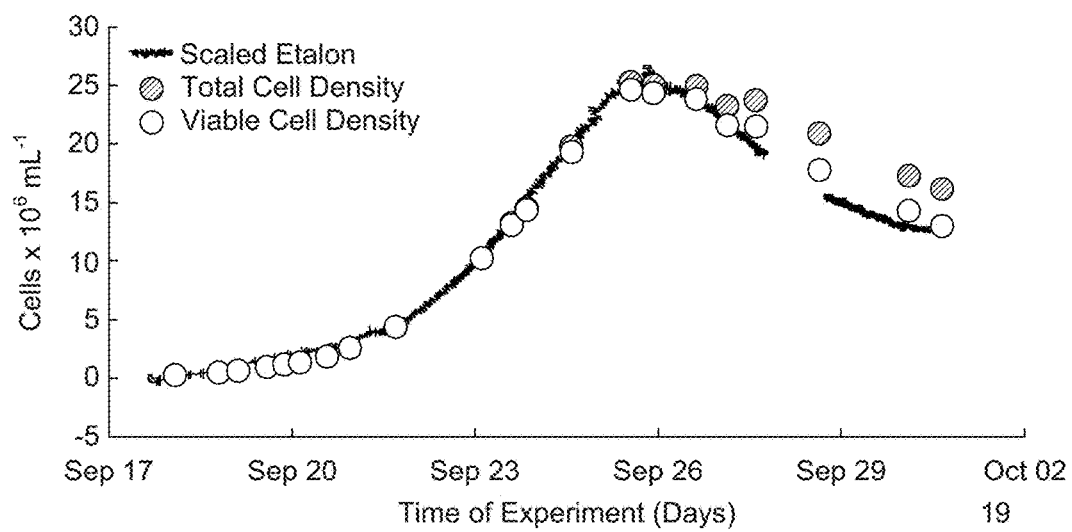
FIG. 6 is a series of plots of the total cell densities and viable cell densities as a function of time obtained by an offline technique in comparison to the viable cell densities as a function of time obtained by an etalon-based arrangement such as described herein.

The results of the FFT conversions performed on the entire data set (obtained at various time intervals) are presented in FIGS. 5A and 5B. When converted to a space domain by FFT, the peak observed was at approximately 0.36 mm. (The detector used in this experiment was obtained from Hamamatsu and had a quoted detector window thickness of 0.35 mm.) Zooming in on the peak (FIG. 5B), shows that the peak changed with time. Comparing the magnitude of the peak with offline calibration points obtained by the different technique of trypan blue (an exclusion dye, whereby the cells are stained and counted using a hemocytometer) generated the plots shown in FIG. 6. The results show that, until the maximum number of cells is reached, the numbers of "viable" and "total" measurements are essentially equal. However, at a certain point, cells begin to die. Even though the biomass remains the "total cell density", the offline counters reported a decreasing viable cell number. The etalon measurement obtained by practicing embodiments of the invention tracked very well with the offline data. Thus, using the etalon's reflective strength appears to capture the subtle change in refractive index due to alive and dead cells.

Some embodiments of the invention are conducted using arrangements and techniques for obtaining samples to be analyzed (e.g., by NIR) such as those described in U.S. patent application Ser. No. 17/006,172, to Hassell et al, filed on Aug. 28, 2020 and incorporated herein by this reference in its entirety, hereinafter "Hassell II".

In one implementation, techniques described herein are practiced with a bioreactor that houses or is a cell culture system for the three-dimensional assembly, growth and differentiation of cells and tissues. The bioreactor can contain cells, culture media, nutrients, metabolites, enzymes, hormones, cytokines and so forth. Techniques described in Hassell II employ a sample tube that can be inserted into a vessel, e.g., a bioreactor or another type of vessel or arrangement used to conduct biochemical or chemical processes. The sample tube for extracting a sample from the bioreactor can be combined or integrated with a sample cell designed for NIR interrogation and analysis. The optical components of the sample cells can be configured as shown in FIG. 1A, using a non-AR coated window.

In another approach for obtaining cell viability data, the sample is analyzed in situ, with measurements being taken within (inside) the reactor, typically without a need to withdraw a sample into a sample or flow cell or into an external (ex-situ) arrangement for taking a reading. This circumvents passing cells through conduits outside the reactor and/or through a pumping system, reducing or minimizing damaging cells during the sampling stage of the experiment.

In an arrangement such as described in U.S. patent application Ser. No. 17/030,032, filed Sep. 23, 2020, and incorporated herein by this reference in its entirety, hereinafter "Hassell III", the analysis can be conducted on an ongoing basis. Cells, for instance, and, if desired, other structures or constituents in the cell culture can be detected, at various time intervals, and the data can be used to assess conditions and, if necessary, adjust or optimize process parameters. Examples of processes that can be monitored include cell growth and/or maintenance protocols conducted in a bioreactor of a suitable design and characterized by a specific volume or dimensions, as known in the art or as developed in the future.

Figure 7:
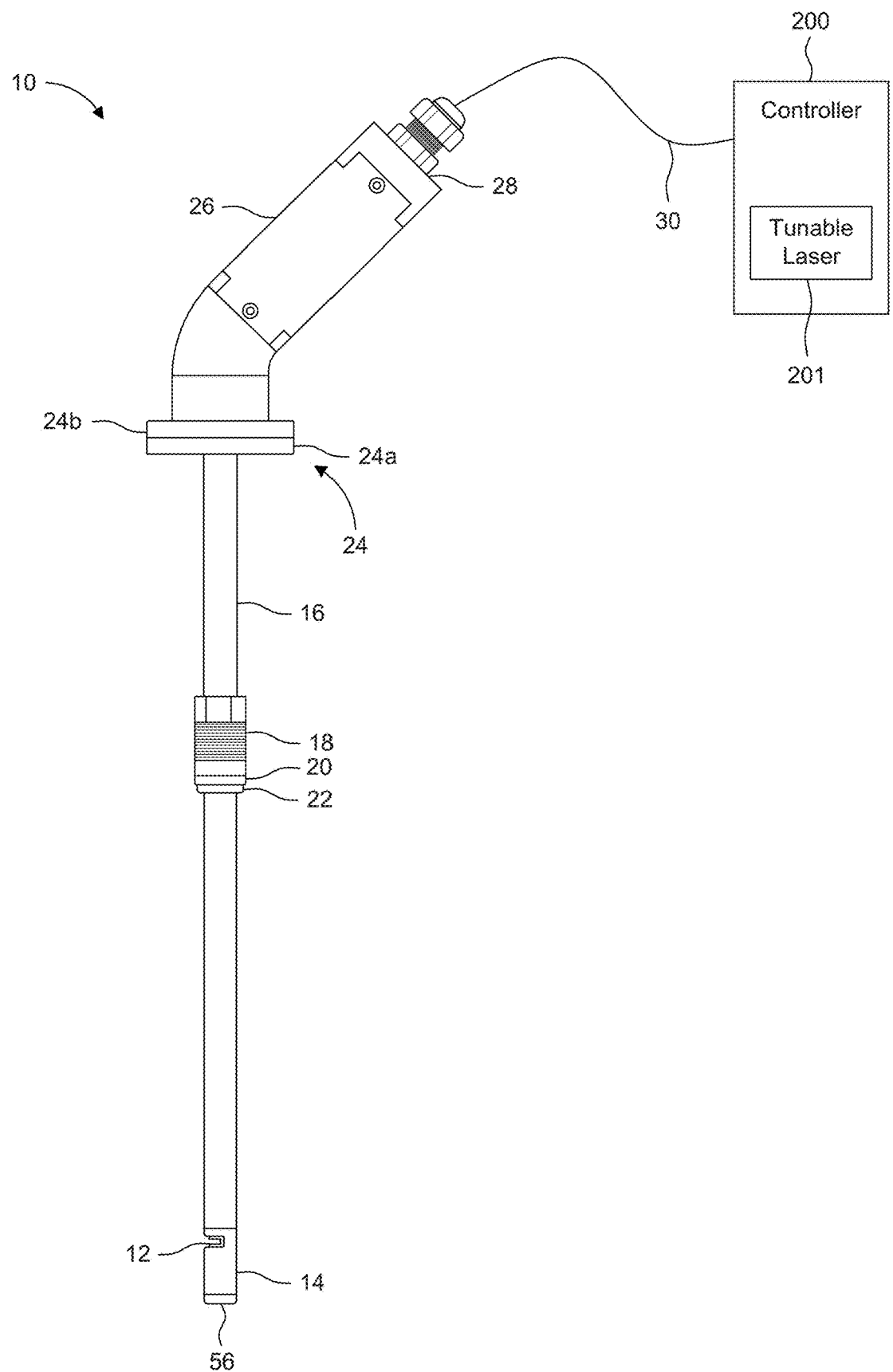
FIGS. 7 and 8 are a side elevation and a partial cross-sectional view of an in-situ probe or components thereof that can be used to monitor viable cells in a bioreactor according to the present invention.
Figure 8:
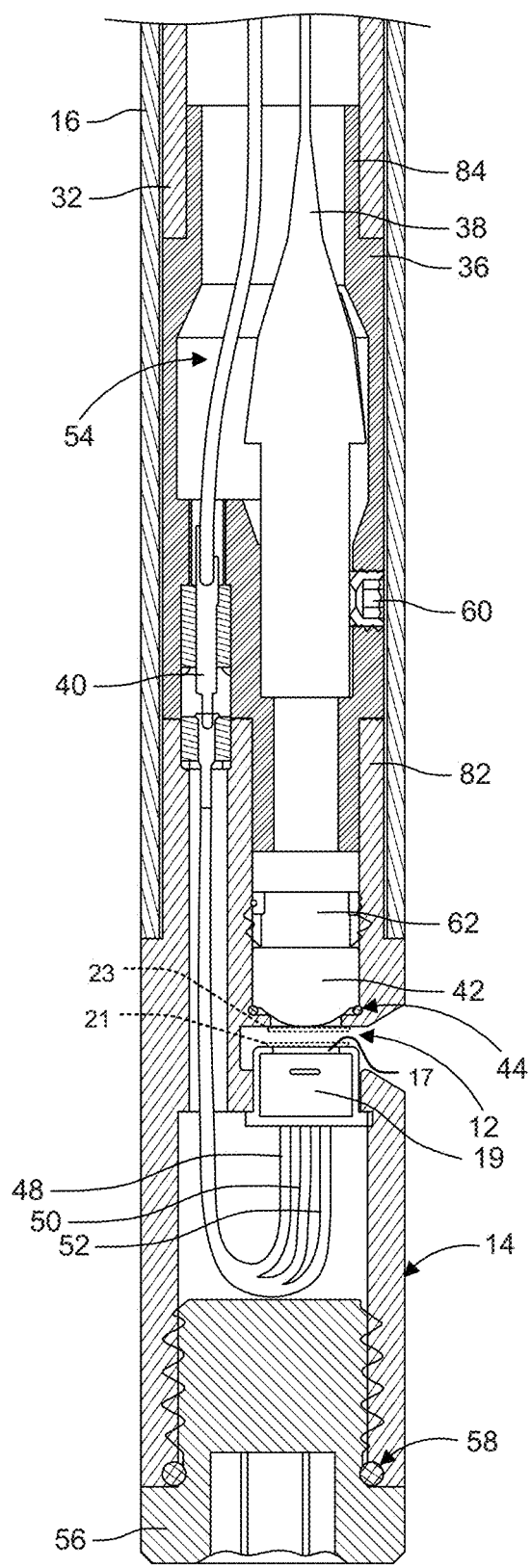

FIGS. 7 and 8, for example, are views of an in-situ probe 10 configured for placing and/or maintaining the tip section 14 of the probe 10 within the bioreactor. The tip section can be made of stainless steel and includes a sample detection area or region 12.

As seen in these figures, the sample detection region 12 is located at a tip section 14 of probe 10 and can be shaped with an indentation formed as further described below. The sample detection area is defined by an optical transmission port and an optical detection port. In this embodiment, the optical transmission port is a focusing lens (or another suitable optical component) or a window optically positioned after the focusing lens. The optical detection port is a photodetector, or a window before the photodetector, facing the lens across the sample detection region 12. Tip section 14 further includes a proximal necked-down portion 82 that is inserted into the distal end of an outer tube 16, e.g., a 12-mm diameter stainless steel tube. The outer surface of the necked-down portion 82 is bonded to the inner surface of the distal end of the outer tube 16. The outer tube 16 is configured to receive an inner tube 32.

Since many bioreactor headplates are equipped with ports for receiving various fittings which can be screwed in, fitting 18, optional Teflon washer 20 and EPDM rubber O-ring 22, or another suitable arrangement, provide a seal on the headplate at the top a bioreactor. In more detail, fitting 18 can be a PG13.5 18 fitting having the standard thread typically used on bioreactor headplates. Optional Teflon washer 20 (which does not provide a seal) can be used as a spacer to ensure sealing on certain bioreactor headplates that may have a deeper threaded section for the PG13.5 fitting. The EPDM O-ring 22 creates the seal between the headplate and the bottom of the Teflon washer 22 as the PG13.5 fitting 18 is tightened.

The dimensions of tip section 14 and the outer tube 16 can be selected according to the size of the reactor. In many situations, the longitudinal distance between the fitting 18 and the sample detection region 12 of the tip section 14 is configured to expose this detection region 12 to the reactor medium being monitored and specifically a portion of that medium that is representative of all of the medium in the bioreactor, rather than possibly unmixed medium along a wall of the reactor. In one illustrative example, the distance between the fitting 18 and the optical detection region 12 is at least 1 centimeter (cm), e.g., at least 2, 3, 4, 5, 10, 15, 20, 25, 30, 35, 40, 45, 50, 55, 60, 65, 70, 75, 80, 85, 90, 95 or 100 cm. Tip section 14 can be smaller, for miniaturized reactor designs, for instance, or larger, for some industrial scale applications.

Flange arrangement 24 can be made (entirely or in part) of stainless steel and includes upper flange 24b, for joining electronic housing 26 to bottom flange 24a. The lower end of tip section 14 is capped by plug 56, made, for instance, of stainless steel. Rubber (EPDM) O-ring 58 provides a leak-tight seal.

Within the distal end of the inner tube 32 is a proximal end 84 of a housing 36. The housing 36 includes elements such as collimator 38 and an electrical connections, e.g., 3-pin POGO connector 40. For analysis, a light beam (generated by a laser 201 in the controller 200) is directed through collimator 38 and focused by lens 42, the latter being seated onto a rubber (EPDM) O-ring 44. From lens 42, typically a molded aspheric lens, light propagates through the bioreactor medium present in a volumetric sample detection region 12 and reaches the packaged photodiode 19, provided, respectively, with anode, cathode and ground wires 48, 50 and 52. These wires serve to transmit signal from the photodiode 19 to a female connector of the tip section 14 to the male connector 40 of the housing 36; from there, the signal follows along wires 54, through tube 32, electronics housing 26, cable gland 28 and wire harness 30, for signal analysis, e.g., by controller 200. In general, during operation, the light from the tunable laser 201 is coupled into the wire harness 30 and specifically optical fiber 124 and travels through the inner tube 32 of be probe. The light exiting from the fiber is conditioned and collimated by the collimator 38 and focused by aspheric lens 42 to propagate through the sample detection region. The transmitted light is then detected by the photodiode 19 after being modulated by the sample in the volumetric detection region 12, which will tend to preferentially absorb some wavelengths relative to others.

In this design, the etalon can be provided in a number of different locations. In one example, the etalon is a non-AR coated window 17 of the detector 19. In another implementation, a separate substrate 21 is located in the volumetric sample detection region 12.

In still another example, two etalon substrates 23, 21 are located between the aspheric lens 42 and the photodiode 17, on either side of the volumetric sample detection region 12.

The controller 200 monitors the response of the photodiode 19 via the anode wire 48, cathode wire 50, and ground wire 52. The detachable electrical connections are made through the 3-pin connector 40. Thus, the controller can resolve the absorption spectra of the sample by monitoring the spectral scanning of the tunable laser over its scan band relative to the time-response of the photodiode 19. Generally, the tunable laser or tunable laser system sweeps its narrow band emission over some region of the electromagnetic spectrum such as the NIR and/or short-wave infrared (SWIR) regions, or portions thereof.

According to the invention, the controller 200 additionally performs a spectral analysis such as by performing a FFT on the response of the photodiode 19 during the spectral scan to resolve the contrast of the one or more etalons and changes in the etalons' contrast. This resolved contrast and contrast changes are then used to determine the presence of viable cells, and the viability of those cells.

In general, it is possible to convey the transmitted light, e.g., via fiber optics, to a photodetector external to the reactor. However, an arrangement in which the detector 19 is part of the in-situ probe exploits signal to noise ratio (SNR) advantages of transmitting electrical signals, e.g., along wires 48, 50, 52 and 54 (relative to directing light transmitted through the sample detection region 12 to an external photodiode detector, via fiber optics).

In typical operation, a desired scan rate can be set using a scanning program executing on the controller 200. In addition to determining cell viability, embodiments described herein include monitoring other analytes, such as, for instance, lactate, glucose, and/or other compounds that might be present in the cell culture.

The sampling and analysis by the controller 200 can be repeated with any desired frequency over any desired time period. For example, viable cells numbers can be measured daily or at intervals of 2, 3 or more days for a week, two weeks, three weeks or longer. The presence of other constituents can be determined every few minutes, e.g., every 5 minutes. Thus, the entire process can be monitored in real time.

Viable cells also can be analyzed in other situations, for example, in the detection of bioburden in wastewater treatment, in protein production in the laboratory or the commercial manufacture of proteins, and so forth.

Techniques such as described herein also have the potential to enter the cell and gene therapy production process and provide important insight into cell quality and therapy development.

Figure 9:
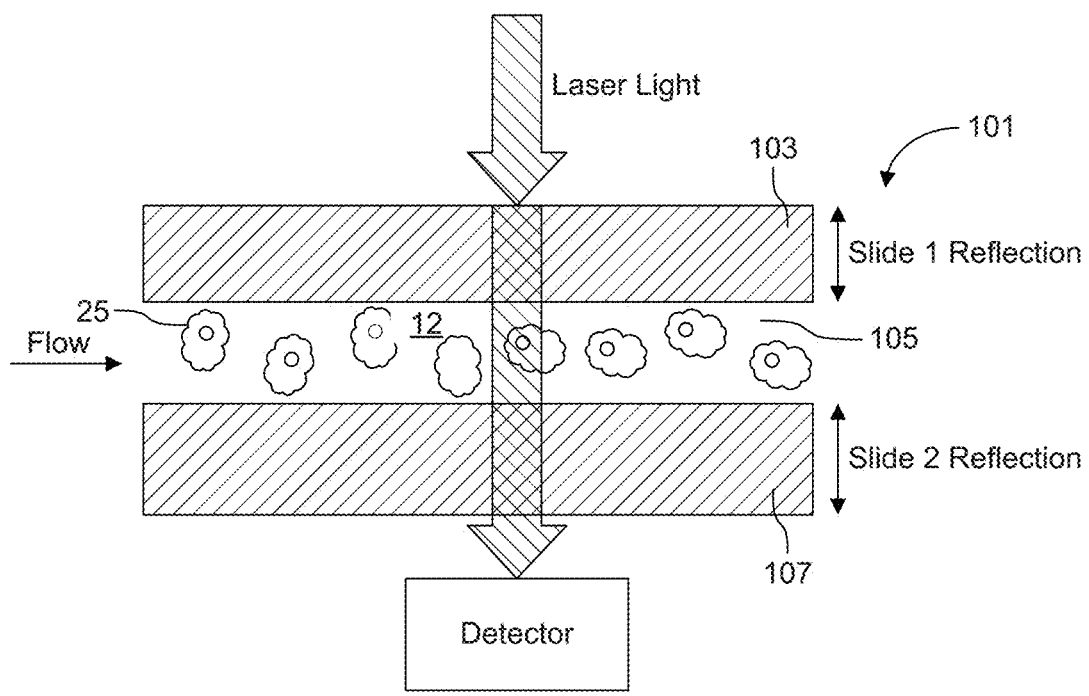
FIG. 9 is a schematic diagram showing a light beam passing through a sample cell in which a cell culture containing cells is sandwiched between two slides forming two etalons.
Figure 10:
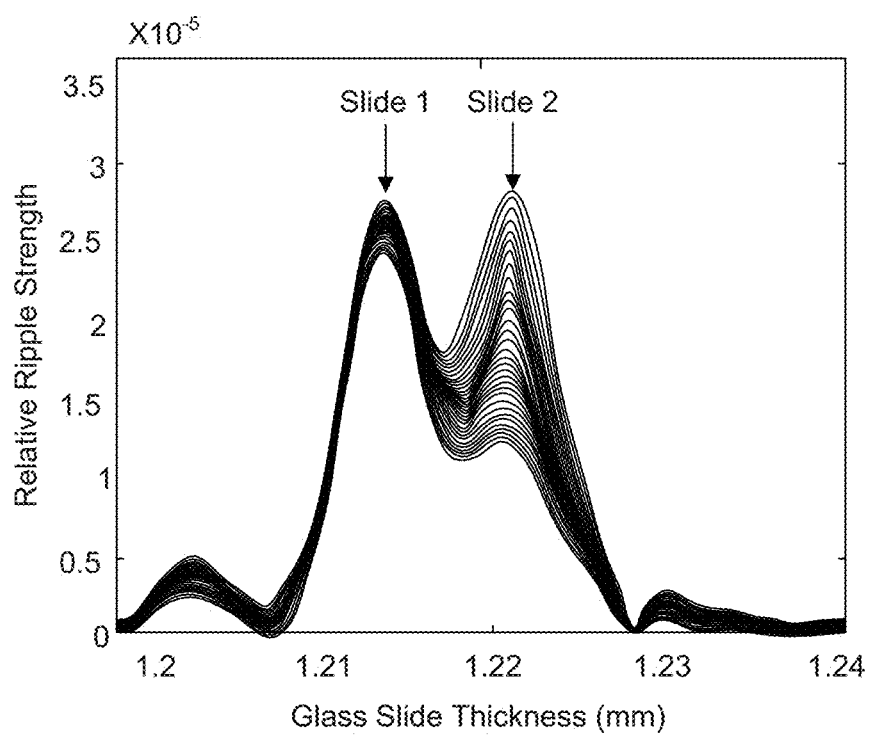
FIG. 10 is a series of plots reflecting the experimentally measured thickness of the slides shown in FIG. 9 in the space domain.

Some applications can provide fine-level information about the experimental set-up employed to analyze samples withdrawn from a reactor into an external flow cell. In one example (see the arrangement of FIG. 9), the flow cell 101 is composed of two parallel microscopic slides with light passing through the first (top) slide 103, which functions in similar fashion to etalon substrate 23 of FIGS. 7 and 8, then through the volumetric sample detection region 12 containing the sample 105 and cells 25 in a culture medium, and exiting the flow cell through a second (bottom) slide 107, which functions similarly to etalon substrate 21 of FIGS. 7 and 8. It was discovered that it was possible to pick out the reflections from the top and bottom surfaces of the flow cell. Since light had not interacted with the cells in the sample, the (first) top slide 103 maintained a more constant signal throughout the experiment. For the second (bottom) slide 107, the light which had already passed through the cells-containing sample decreased and tracked the index shift of the fluid to a larger extent. This approach can also reveal any error in the manufacture of the slides, as illustrated in FIG. 10. Although the two slides were specified to have an identical thickness, the data revealed that they were slightly off.

In other aspects, the invention can also provide information concerning other structures within the fluid such a level of aggregation encountered during the preparation of proteins, such as, for instance, monoclonal antibodies, IgG, IgA, IgM, TNF-alpha, IFN-gamma, to list a few. In one illustrative example, the invention is applied to the production of human or humanized IgG monoclonal antibodies (e.g., IgG1, IgG2 or IgG4).

Specific embodiments relate to detecting and, preferably, quantifying protein aggregates. As used herein, the term "protein aggregates" refers to oligomers such as protein dimers, trimers, higher oligomers, polymers, clusters, filaments, agglomerated aggregates and/or other assemblies formed from the monomeric form of the protein. A study of various possible aggregated states that can be adopted by proteins, either as folded molecule or unfolded/partially-unfolded ones, is provided by C. J. Roberts in *Protein Aggregation and Its Impact on Product Quality*, Curr. Opin. Biotechnol., 2014 December; 0: 211-217, published online 2014 Aug. 28, PMC4266928, which is incorporated herein by this reference. Factors identified in this publication as contributing to whether or how rapidly aggregation can occur include solution conditions (pH, salt concentration and/or the nature of salt employed, the amount and type of osmolytes present, the use of amphiphilic molecules such as surfactants); temperature; pressure; air-water interfaces; other bulk interfaces (e.g., between water and stainless steel), and so forth.

For example, when heated, some proteins will undergo aggregation, first forming soluble assemblies (such as dimers, trimers, other small oligomers), which can then progress, often rapidly, to insoluble large or very large fibrils. Since, in practical terms, it might be possible to control the formation of insoluble protein assemblies (by adjusting solution conditions, for example), some embodiments described herein focus on detecting soluble protein aggregates. Techniques described herein may also be employed to detect larger, insoluble species, e.g., contaminants.

Monitoring protein aggregates can be conducted in conjunction with detecting and, preferably, quantifying amounts of the protein in its monomeric, also referred to herein as "unaggregated", form. Measuring both unaggregated protein and protein aggregates can be simultaneous or nearly simultaneous.

In one illustration, an initial protein product (obtained, for instance, by separating cells from their culture medium) is purified and concentrated in a single "capture" operation based on protein A chromatography. While Staphylococcal protein A can provide very efficient binding to IgG molecules, elution of the product typically relies on lowering the pH. Since acidic conditions and abrupt changes in pH have been associated with aggregation (see, e.g., A. R. Mazzer et al., *Protein A Chromatography Increases Monoclonal Antibody Aggregation Rate During Subsequent low pH Virus Inactivation Hold*, J. Chromatogr. A, 1415:83-90, Oct. 9, 2015), assessing the degree of aggregation at this point in the production process can be important.

Thus, techniques described herein can be particularly useful when conducted on fluid eluted from protein A columns. Other applications pertain to streams that are cleaner and/or purer, such as those that can be produced by cation exchange columns (CEX), for example. Another use is ultrafiltration (UF) and diafiltration (DF), which are steps in downstream processing for product concentration and buffer exchange. In an exemplary process, UF/DF precede chromatographic columns with this UF/DF pre-treatment preparing the product for the subsequent chromatography stage. The columns might be operating under different pH or molarity conditions. Typically, the UF/DF steps concentrate and resuspend the product in the correct buffer before introduction into the columns.

A useful approach for assessing protein concentrations takes advantage of water exclusion, as illustrated in FIGS. 11A, 11B and 11C.

FIG. 11A, for example, presents a series of absorbance plots obtained at increasing concentrations (from 10 milligrams/milliliter (mg/mL) to 100 mg/mL) of a protein such as bovine serum albumin (BSA). Although a protein-specific NIR band occurs around 1700 nm, the water exclusion signal at around 1440 nm is stronger, providing an increased dynamic range. More specifically, in the 1440 nm region, absorption caused by the presence of water decreases proportionally with the increasing protein concentrations (as more and more water becomes replaced or "excluded" by the protein). As less and less water absorption takes place, the transmission at 1440 nm (a band characteristic of the water background) will increase proportionally.

FIG. 11B is a plot correlating the NIR light transmission at 1440 nm, as a function of protein concentration. As seen in this plot, the transmission, which at this wavelength is characteristic of water, increases proportionally with increasing amounts of water-replacing protein (and the corresponding decreases in absorption by the water background). A similar trend is seen in FIG. 11C, which plots the transmission at 1440 nm (characteristic of the water background) for protein concentrations between 0 and 10 mg/mL.

The water exclusion techniques described above can be applied or adapted to nonaqueous systems and/or to structures other than proteins.

In practice, the presence of protein changes the FFT signal relative to a matched culture medium that is free of protein. In addition, the magnitude of the peak observed with respect to the length scale can reflect changes in protein aggregation. Thus, in comparison to the peak observed in the absence of any type of protein (background only), the FFT conversion to a space domain reveals a peak that is smaller in the presence of monomeric protein and smaller still when both unaggregated as well as aggregated protein forms are encountered. In short, the phase-front distortion produced by the protein is exhibited in a lowering of the contrast of the window etalon. This distortion is accentuated by the formation of protein aggregates (observed as a further lowering of the contrast of the window etalon).

To illustrate, one example employed two water-based solutions containing, respectively, less than 15% dimer and ~25% dimer/trimer bovine serum albumin (BSA). The solutions were prepared as described by D. Molodenskiy et al., in *Thermally Induced Conformational Changes and Protein—Protein Interactions of Bovine Serum Albumin in Aqueous Solution under Different pH and Ionic Strengths as Revealed by SAXS Measurements*, Phys. Chem. Chem. Phys., 2017, 19, 17143-17155, DOI: 10.139/c6cp08809k and used Tris (hydroxymethyl) aminomethane (THAM) hydrochloride at 10 mg/mL BSA and 25° C. In more detail, one solution contained 50 mM Tris-HCl buffer, at pH 9, 0.1M NaCl (<15% dimer), while the other contained 50 mM Tris-HCl buffer, pH 7.4, 0.5M NaCl (~25% dimer/trimer). Multiple (1,000 in these examples) scans were taken for: (i) a background solution containing no protein, either in monomeric or aggregated form; (ii) the first solution (<15% dimer); and (iii) the second solution (~25% dimer/trimer species).

Analysis of the etalon signal (magnitude) for each of the wavelength 1,000 scans generated the histogram of FIG. 12. Regarding the data presented in this figure, the mean of the distribution was subtracted to account for the change in salt concentration. Some of the outliers far to the left are thought to indicate potential scans with high densities of proteins/higher molecular weights. The distributions for solutions with protein seem to be bimodal and skewed. Possibly, the emergence of a second mode is derived from the higher molecular weight protein addition.

If the variation in background is the noise floor, or just what a clean stream distribution appears to be like, then, setting a threshold at the lower limit can establish a percent of higher molecular weights than the baseline monomer. A threshold set at approximately −2e5, as seen here, yielded percent aggregates of 11.5% for the low salt condition and 24.7% for the high salt condition.

Figure 13A:
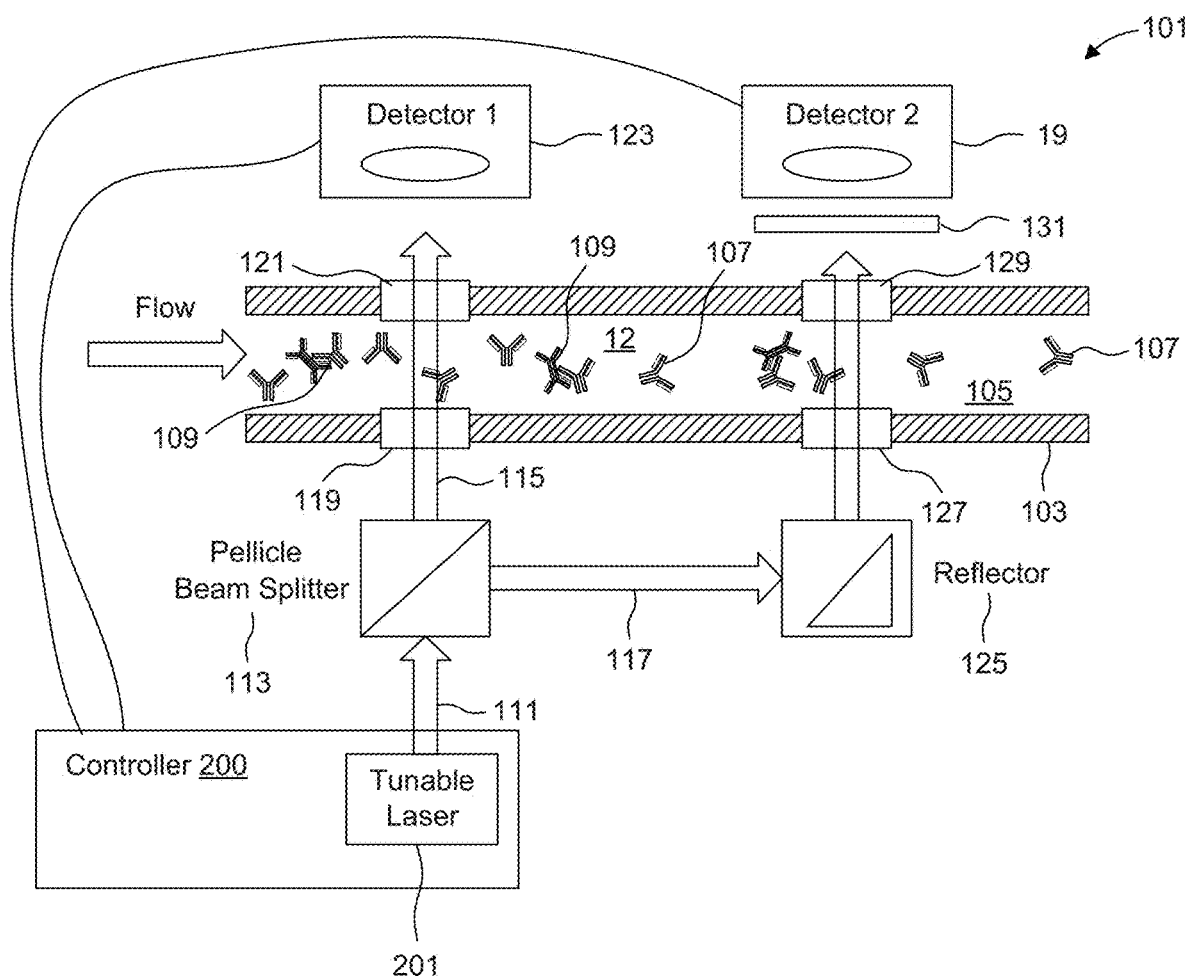
FIG. 13A is a diagram of an arrangement that can be used to detect structures such as monomeric and aggregated proteins in a flowing protein-containing medium and/or assessing cell viability.

Some embodiments of the invention are conducted in a flowing system. FIG. 13A, for example, shows a system for performing simultaneous absorption measurements, e.g., in the near infrared (NIR) region, along with structural analysis such a cellular and/or protein aggregation analysis.

Here, a flow cell 101 includes a conduit 103, e.g., a pipe, tube, microfluidic channel, etc. Conduit 103 supports the flow (see arrow) of fluid 105, containing structures such as protein monomers 107, as well as protein aggregates 109 in a suitable medium, often water or water-based. Fluid 105 can contain cells or can be a fluid that has been obtained, for instance, after the cells had been filtered out from the culture medium. In one implementation, flowing fluid 105 is derived from a protein A column.

Collimated light 111 or light propagating in a fiber, in the NIR region of the electromagnetic spectrum supplied from a suitable laser source 201, such as, for instance, an Axsun Duo instrument (producing a narrow linewidth that is wavelength swept over the spectral band of 1350 nm to 1800 nm region), is directed to beam splitter 113 (a pellicle mirror, for example), which generates first beams 115 and second beam 117. Beam 115 traverses window 119, fluid 105 flowing through conduit 103, then window 121, to reach a first, absorption detector 123, suitable for spectrometric measurements in the NIR region. Other embodiments employ a vertical cavity surface emitting laser, or VCSEL, as a tunable light source.

Second beam 117, redirected by reflector 125, passes through window 127, across the volumetric sample detection region 12 including solution 105 flowing through conduit 103, and window 129. It then traverses etalon window 131, which could be a separate window or a detector window as described previously, to reach second, structure analysis, detector 19.

Windows 119, 121, 127 and 129 can be made of quartz or another material that is optically transparent in the NIR region and are configured to prevent reflections, by using an AR coating, for example. In contrast, etalon window substrate 131 does not employ an AR coating to function as an etalon, setting up the internal reflections discussed above. In many implementations, etalon window 131 is inserted between window 129 and second detector 19. In an illustrative example, it has a thickness of about 100 µm and resembles a microscope slide cover.

Figure 13B:
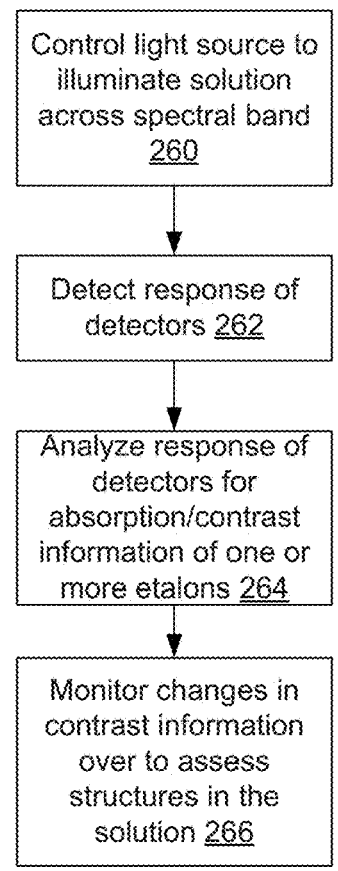
FIG. 13B is a flow diagram illustrating the operation of the controller.

FIG. 13B is a flow diagram illustrating the operation of the system and the controller 200.

In more detail, the controller 200 activates the tunable laser 201 to spectrally analyze the solution 105 in step 260. Often, the controller 200 controls the tunable laser 201 to collect several spectral scans of the solution.

At the same time, the controller 200 monitors the response of both detectors 123, 19 in step 262.

Often, in step 264, the controller 200 averages the response of the spectrometric measurement detector 123, over several scans, such as more than 5 scans, in order to resolve absorption spectra of the solution. In the case where the light source is a tunable laser, the averaging occurs in the time domain.

The controller 200 additionally monitors the response of detector 19 and analyses its response to resolve contrast information of the etalon 131, and possibly a second etalon, to assess the structures in the solution in step 266. Typically, the response of the detector 19 is not average in the time domain. Instead, the controller performs the Fourier transform of the response of the detector for each spectral scan and then possibly averages the Fourier transform from several scans. The high spectral or spatial frequency peaks of the Fourier transformed response are analyzed to assess the contrast information of the one or more etalons, and, monitored over time, to assess structures, such as cells or proteins in the solution.

Figure 14:
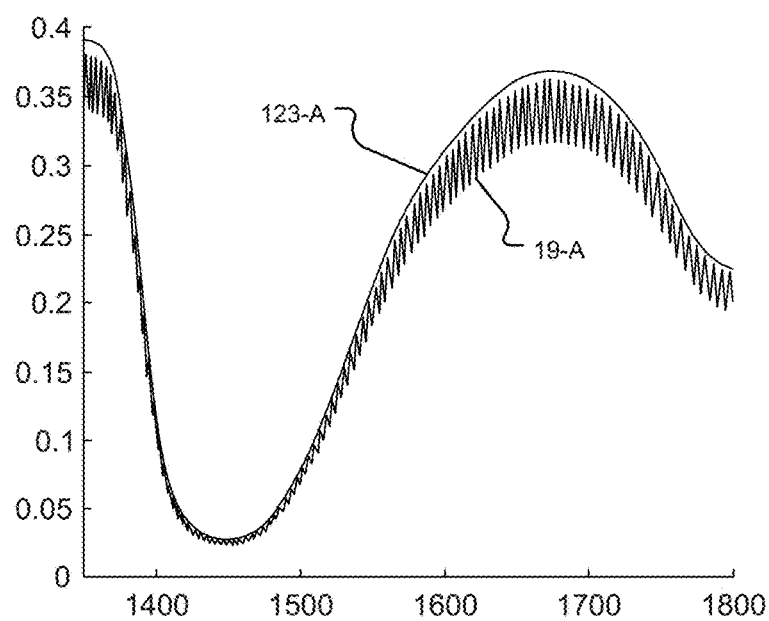
FIG. 14 displays the high frequency signal generated by the etalon and submerged in the single beam transmission (in the region of 1350 to 1800 nm) of a protein-containing medium.

Shown in FIG. 14 is an illustrative spectral scan (in the region of 1350 to 1800 nm, represented by the curve) obtained by the detectors 123, 19 as the tunable laser is swept through the scan band of about 1350 to 1800 nm. The smooth line 123-A is the response of the first, absorption detector 123. Line 19-A exhibiting the high frequency structure is the response of the second, structure analysis, detector 19. This high frequency structure corresponds to the contrast of the etalon 131 superimposed on the contour of the absorption spectra of the solution.

In some cases, the response of the first detector 123 enables the controller 200 to measure the concentration of a given protein (in its monomeric form) by monitoring the NIR absorbance (or transmission) signal at a wavelength associated with a spectral feature characteristic of the protein. The NIR absorbance spectra are resolved by the controller 200 as the time-response of the first detector as the tunable laser 201 is wavelength swept through its spectral scan band. As one example, a protein specific absorbance signal might occur around 1700 nm. The known linear correlation between absorbance (around 1700 nm in this case) and concentration can be used to calculate protein amounts.

For cases in which fluid 105 is water-based, another useful approach can take advantage of the "water exclusion" signal, which will linearly correlate with the amount of protein present against a water background. Measurements can be obtained in a region associated with one of the NIR bands characteristic of liquid water. As described above with reference to FIGS. 11A, 11B and 11C, when increasing amounts of water-replacing protein are added, the water absorbance signal at a water-specific wavelength (e.g., around the 1450 nm band characteristic of pure liquid water) will decrease proportionally.

At the same time, the controller 200 analyzes the response of the second detector 19 to analyze the structures, such cells or proteins, in the medium.

Many of the embodiments described herein employ transmission spectrometry. Some situations, however, can benefit from the use of transflection (also known as transflectance) techniques. Such techniques can be applied not only in the context of protein aggregations but also in monitoring other components present in a system, in studying processes conducted in a bioreactor, for instance. (Illustrative arrangements relying, respectively, on transmission and transflection principles are presented in FIGS. 15A and 15B, as further described below.)

Figure 15A:
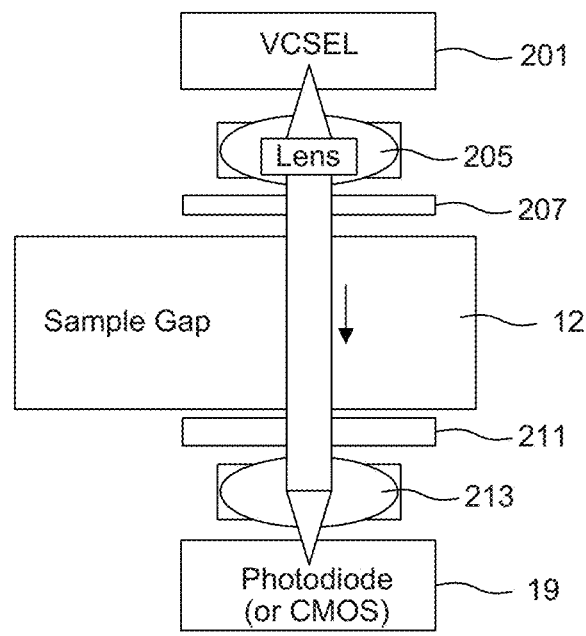
FIG. 15A is a schematic diagram of an arrangement configured for transmission spectrometry and employing two etalon windows of different thicknesses.

Shown in FIG. 15A is an arrangement in which the tunable light source 201 is a tunable vertical cavity surface emitting laser or VCSEL. Various types of VCSELs are known or are being developed, covering continuous wavelength (CW), quasi CW or pulsed applications. Common available center wavelengths are 830, 976, 1064 nm. The tunable VCSELs are then tunable in a scan band of typically greater than 30 nm and preferably greater than 50 nm in a spectral band around the center wavelength. Other wavelengths within the range between 630 and 1064 nm can be supplied in some cases. Using VCSELs in conjunction with a low-cost silicon photodetector may push the desirable wavelength to the long end of the spectrum, in the range between 800 and 900 nm, for example. In many cases, VCSELs supply superior spectral properties relative to other IR sources such as high-power LED and edge-emitting laser diodes (EELD). For example, NIR VCSELs often present a narrow linewidth laser emission, a stable wavelength and can be less wavelength dependent on temperature effects. In addition, due to their nature, VCSELs can be associated with a lower cost for being manufactured in a package.

From source 201, light, in the NIR region, for instance, is focused by lens 205 and propagates as shown by the arrow in a direction normal or perpendicular to etalon window 207, which functions such as etalon substrate 23 of FIGS. 7 and 8. The light traverses volumetric sample detection region 12 (which can be defined by AR windows such as windows 127 and 129 in FIG. 13A, or the probe of FIGS. 7 and 8). The transmitted light passes through etalon window 211 (which functions such as etalon substrate 21 of FIGS. 7 and 8), is focused by lens 213 and detected by sensor 19, e.g., a photodiode or a complementary metal oxide semiconductor (CMOS) detector. Some embodiments utilize a design in which etalon window 211 and the photodiode or CMOS sensor are integrated in a detecting device, with etalon window 211 being the detector window. In other embodiments, etalon window 211 can be a standalone, non-AR coated window of substrate, similar to a microscope slide cover.

Figure 15B:
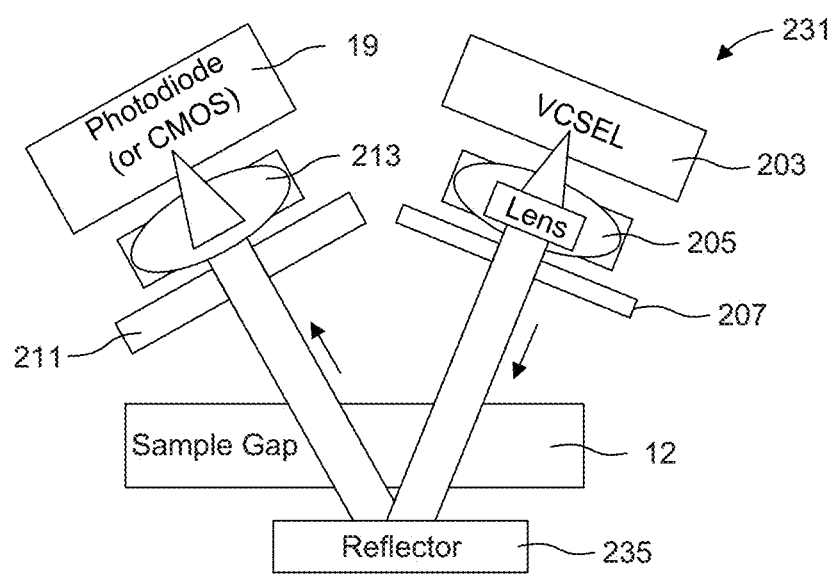
FIG. 15B is a schematic diagram of an arrangement configured for transflection spectrometry and employing two etalon windows of different thicknesses.

FIG. 15B shows a transflection arrangement in which light (in the NIR region, for instance) is generated by source 201 such as the VCSEL described above, focused by lens 205 and is directed toward the volumetric sample detection region 12 at an angle of incidence (angle between the ray incident to a surface and a direction perpendicular to the surface) that is other than 0, such as 45 degrees, +/−20 degrees. The light passes through etalon window 207 and then through volumetric sample detection region 12. Often the sample gap is defined by a flow cell with the sample flowing through its length. It encounters reflector 235, e.g., a NIR mirror, or another suitable optical component that reflects the transmitted light back through region 12, directing it to etalon window 211, lens 213 and sensor 19. In comparison to the transmission arrangement, this transflection arrangement 231 provides an increased pathlength as light passes twice through the region 12. In addition, both the photodiode 19 and the VCSEL 201 are on the same side of the flow cell.

In both arrangements, etalon window 207 (positioned optically before the sample found in the sample gap) can be omitted as seen, for instance, in the embodiment of FIGS. 3A and 3B. Adding etalon window 207 in front of (or before) the light traverses the sample, however, can provide a control (baseline) signal for calibration purposes. For example, if the two etalon windows (207 and 211) have different thicknesses, the frequencies established in etalon window 207 and in etalon window 211 will be different and the signals from the two can be resolved by the controller 200 based on the response of the detector 19 as being (essentially) unaffected by one another.

While in the embodiments of FIGS. 15A and 15B, the etalon window 207 (before the sample) is the thinner etalon window, other arrangements can be employed. For instance, the thinner etalon window can be positioned after the sample. In some implementations, the ratio of the thickness of etalon window 207 to that of window 211 is within a range of from about 1.0:0.1 to about 0.1:1.0.

Figure 16A:
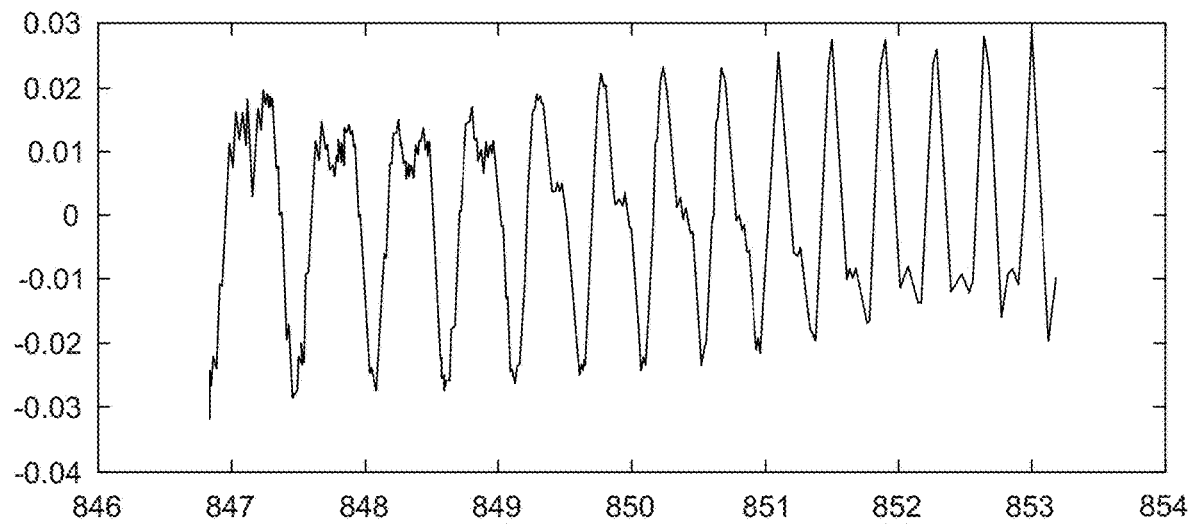
Figure 16B:
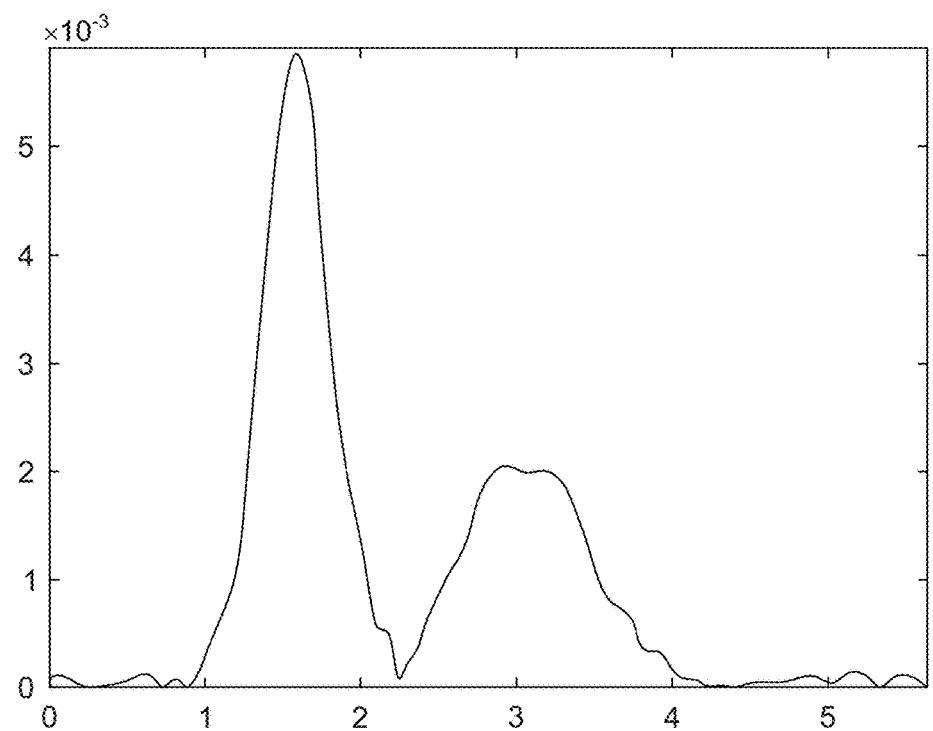

To illustrate the separation of the signals obtained using two etalon windows of different thicknesses, FIG. 16A is a plot (the x axis corresponding to wavelength in nanometers) obtained at the detector for etalon window 207 (positioned before the sample and having a thickness of 3.0 millimeters (mm)) and etalon window 211 (after the sample, having a thickness of 1.5 mm). FIG. 16B further resolves the signals of FIG. 16A, and shows the two frequency components in the signal of FIG. 16A obtained by performing a Fourier transform of the signal of FIG. 16A.

Figure 15C:
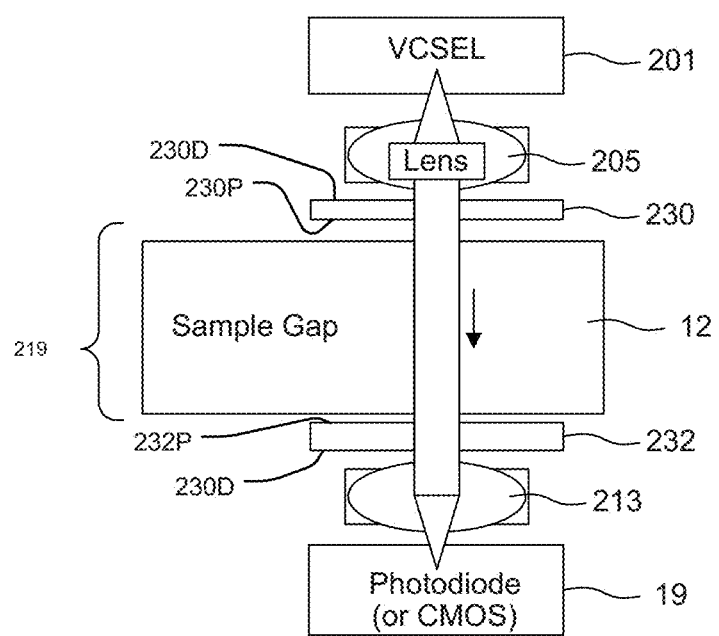
FIG. 15C is a schematic diagram of an arrangement in which the volumetric sample detection region is within the etalon.

FIG. 15C shows still another embodiment in which the volumetric sample detection region 12 is within the etalon. Here, the tunable light source 201 is a tunable VCSEL or other type of laser.

The light from the source 201 (which can be a VCSEL such as described above), is focused by lens 205 and propagates to a first mirror substrate 230. In this example, the side 230D of the first mirror substrate 230 that is distal to the detection region 12 is AR coated. On the other hand, the side 230P of the first mirror substrate 230 that is proximal to the sample detection region 12 is reflective, by being, for instance, uncoated or coated with a reflective coating to provide reflection by the index mismatch between the material of the substrate 230 and the surrounding media.

The transmitted light then passes through the region 12 and a second mirror substrate 232, is focused by lens 213 and detected by sensor 19, e.g., a photodiode or a complementary metal oxide semiconductor (CMOS) detector.

Here also the side 232D of the second mirror substrate 232 that is distal to the detection region 12 is AR coated. The side 232P of the second mirror substrate 232 that is proximal to the detection region 12 is reflective (by being coated with a reflective coating or uncoated) to provide reflection by the index mismatch.

As a consequence, in this embodiment, the etalon exists between the proximal side 230P of the first mirror substrate 230 and the proximal side 232P of the second mirror substrate 232. Thus, the detection region 12 is within the etalon 219 established between surfaces 230P and 232P.

Finally, the first mirror substrate 230 and the second mirror substrate 232 are aligned to be parallel to each other.

This configuration having a combined detection region/etalon is applicable to other embodiments herein. For example, the two etalon substrates 23, 21 of FIG. 8 are coated as described with respect to the first mirror substrate 230 and the second mirror substrate 232, i.e., single sided mirror coatings, in one implementation, and aligned to be parallel to each other. Thus, the etalon is established around the region 12.

The invention is further illustrated by the following non-limiting examples.

Figure 17:
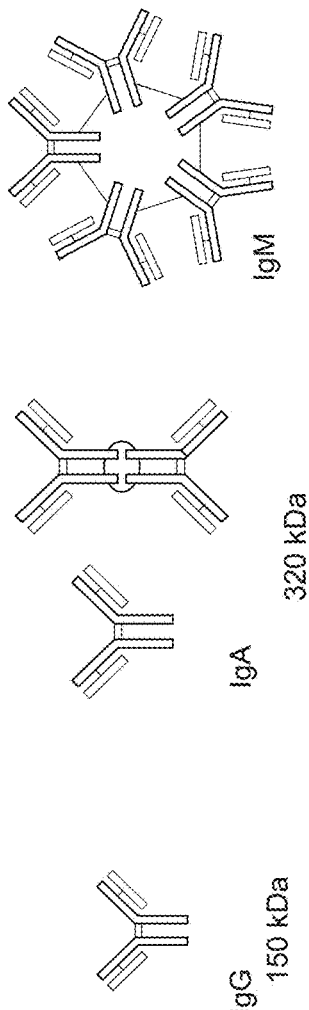
FIG. 17 depicts proteins of different sizes or atomic masses used in feasibility studies presented below.

Proteins employed in these examples included a light protein, IgG (150 kDa), a heavy protein, IgM (750 kDa), and a protein of an intermediate mass, IgA (320 kDa). As seen in FIG. 17, IgG represents a monomeric protein, IgM a highly aggregated protein and IgA a protein dimer.

Figure 18:
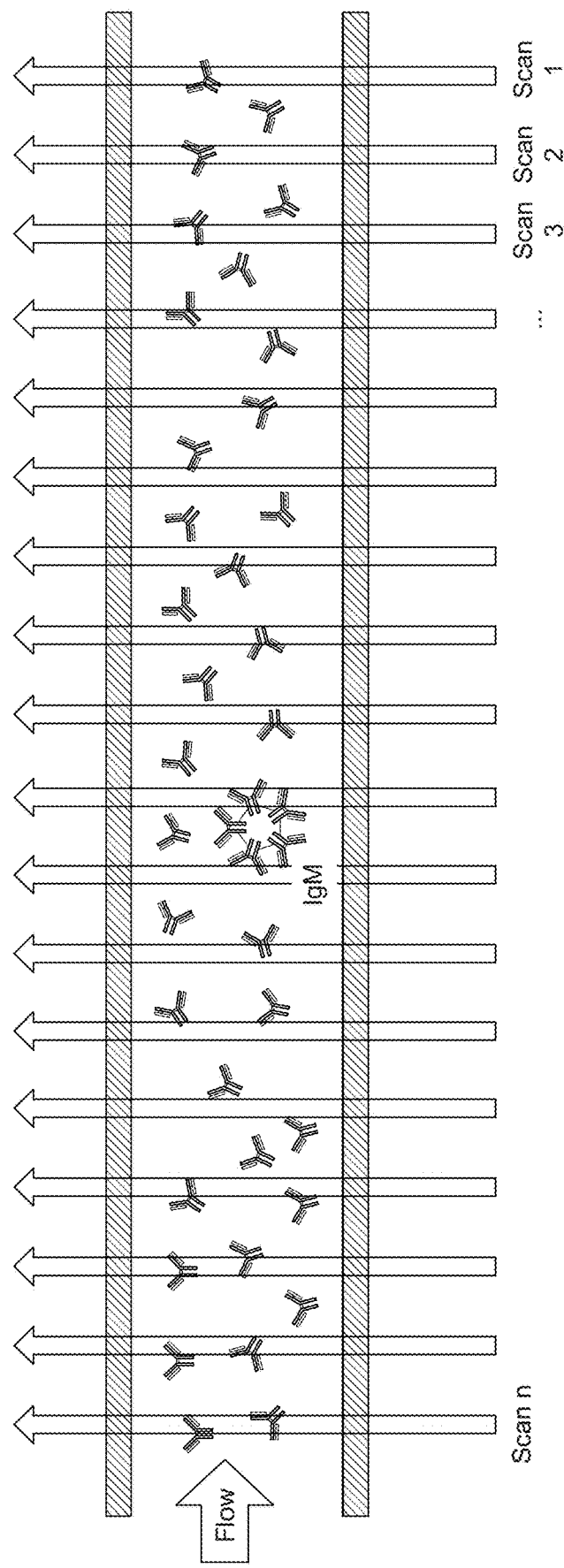
FIG. 18 is a diagram showing the type of protein detected in various scans.

In general, experiments were designed considering that, for a larger protein concentration of 1% and a sampling of the entire fluid, 1% of the scans (1 in 100) should present a detectable signal. With parameters such as flowrate, beam size, etc. not tuned, it is possible that multiple scans will have the same protein in the scan. A schematic representation of multiple scans (1 through n) performed on a sample, containing small proteins IgG and a small concentration of a larger protein such as IgM, flowing in the direction of the arrow, is presented in FIG. 18.

Example 1

This feasibility experiment for detecting IgM in an IgG solution employed a "slow" scanning technique, over time intervals of at least one minute, typically over a time interval of a few, e.g., 3, 4, 5, 6, 7, 8, 9 or 2, 10 minutes. The protocol included preparing an aqueous solution of 1 milligram per milliliter (mg/mL) IgG in phosphate buffered saline (PBS), the IgG acting as purified monomer, followed by adding 1% of the heavier protein IgM (v/v also in PBS). The solution was recirculated through a flow cell and closed loop system, such as, for example a Hellma 1 mm pathlength flow cell (Hellma article #170-000-1-40) with a peristaltic pump (Cole-Palmer Masterflex®).

Figure 19A:
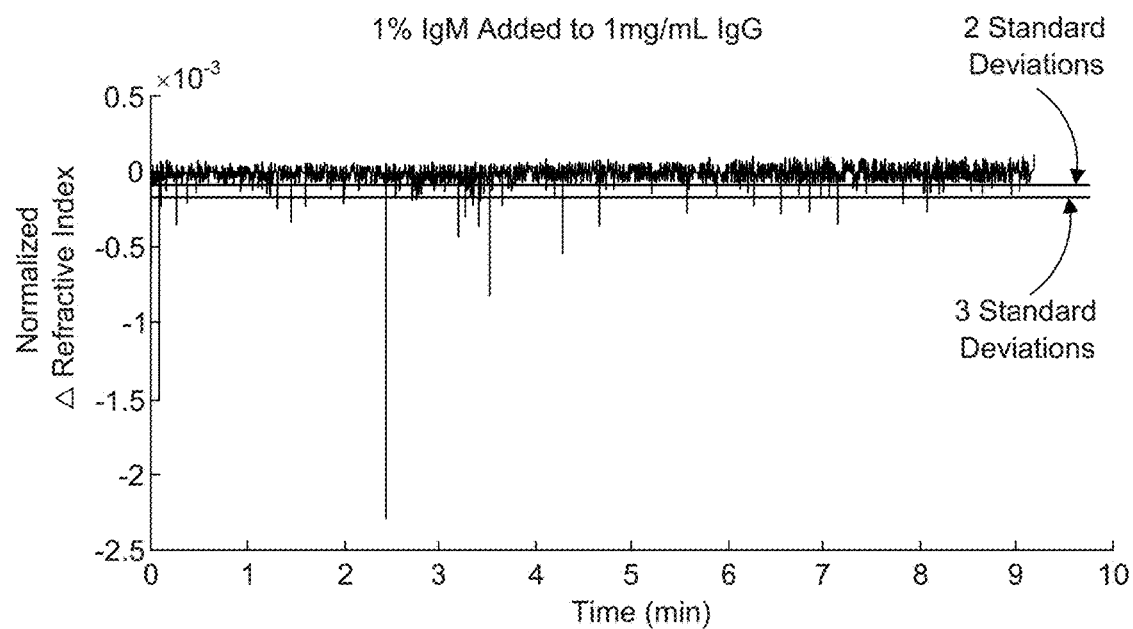
FIG. 19A is a series of plots for a 1% IgM in a 1 mg/mL IgG solution showing the normalized change (A) in refractive index as a function of time at various standard deviations.
Figure 19B:
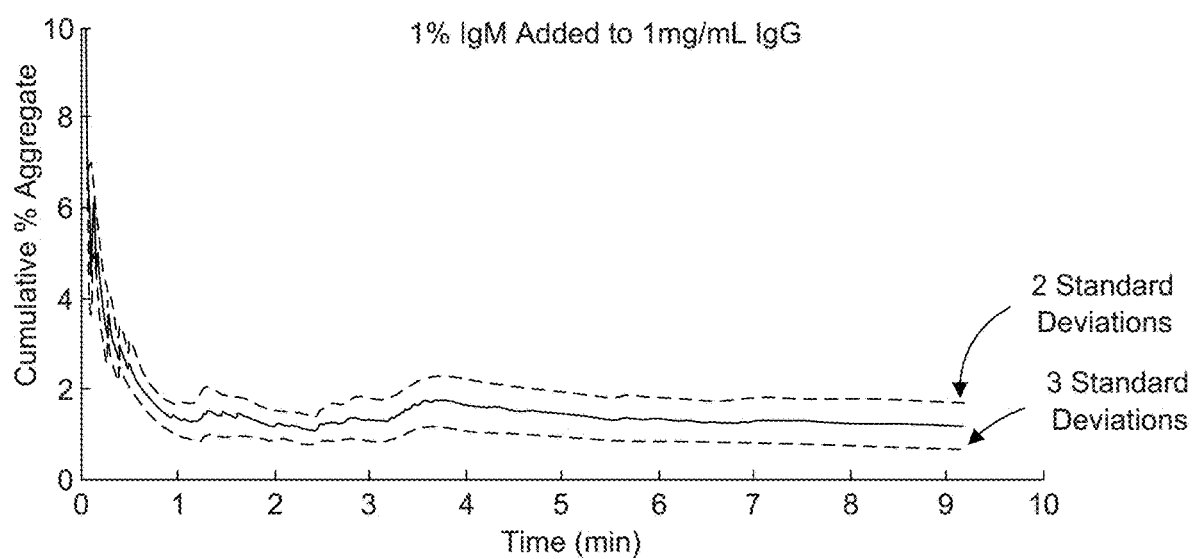
FIG. 19B is a series of plots for the 1% IgM in a 1 mg/mL IgG solution showing cumulative % aggregation as a function of time at various standard deviations.

The number of detected events divided by the number of scans was expected to converge on the correct percentage of aggregates. Standard deviation (STD) was employed to tune event detection. STD×2.75 was determined as threshold for event detection (tuning) and was obtained empirically from 1% spiking runs. The normalized change (A) in refractive index at various standard deviations as a function of time is shown in FIG. 19A, while the cumulative % aggregation (at various standard deviations) as a function of time is shown in FIG. 19B.

The threshold for event tuning determined as described above was then applied to a situation in which 2% of IgM was added to a 1 mg/mL solution of IgG.

Figure 20A:
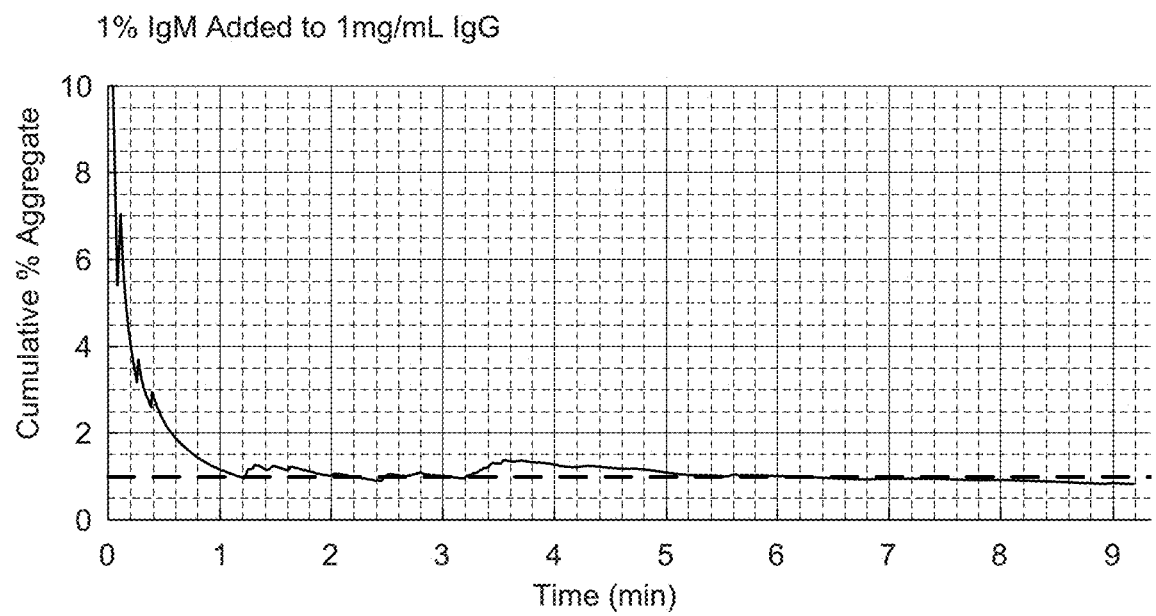
FIGS. 20A and 20B are cumulative % aggregation as a function of time plots for, respectively, 1% IgM and 2% IgM added to a 1 mg/mL IgG solution.
Figure 20B:
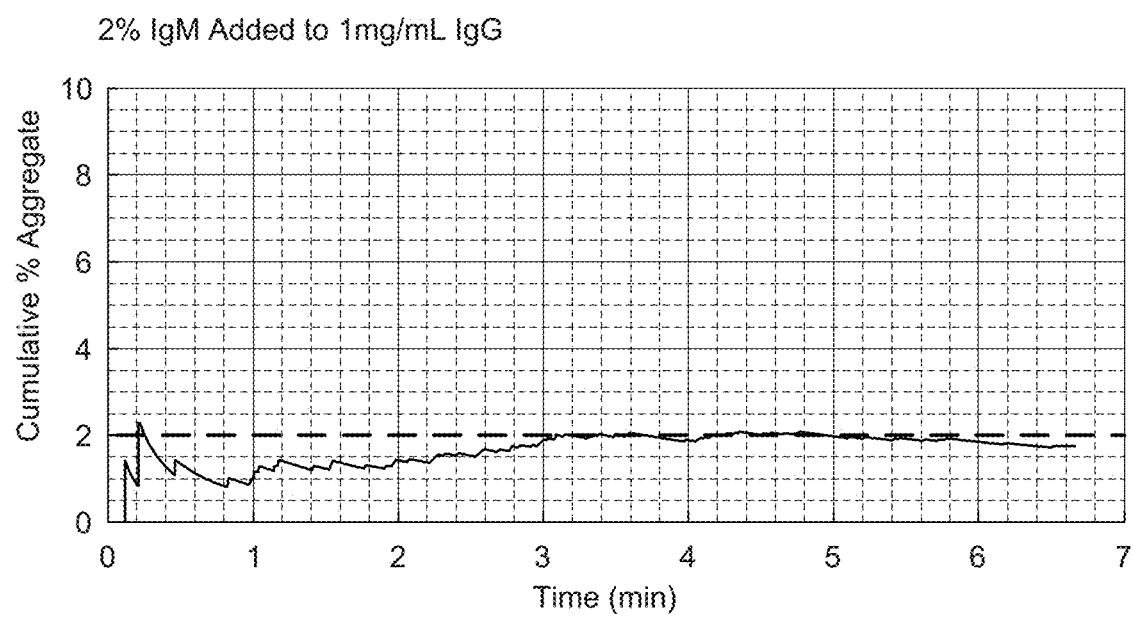

The cumulative % aggregation as a function of time for the 1% IgM sample and the 2% IgM sample, at 2.75 STD, is presented, respectively, in FIGS. 20A and 20B.

Example 2

As in the protocol described above, this feasibility study for detecting IgA in an aqueous IgG solution in PBS employed a solution containing 1 mg/mL of IgG, with IgG acting as a purified monomer. 1% of IgA (simulating a dimer) was added and the resulting solution was recirculated through a flow cell and closed loop system, as in Example 1. Once properly mixed, the number of detected events, divided by the total scans converged on the correct percentage of aggregates.

Figure 21:
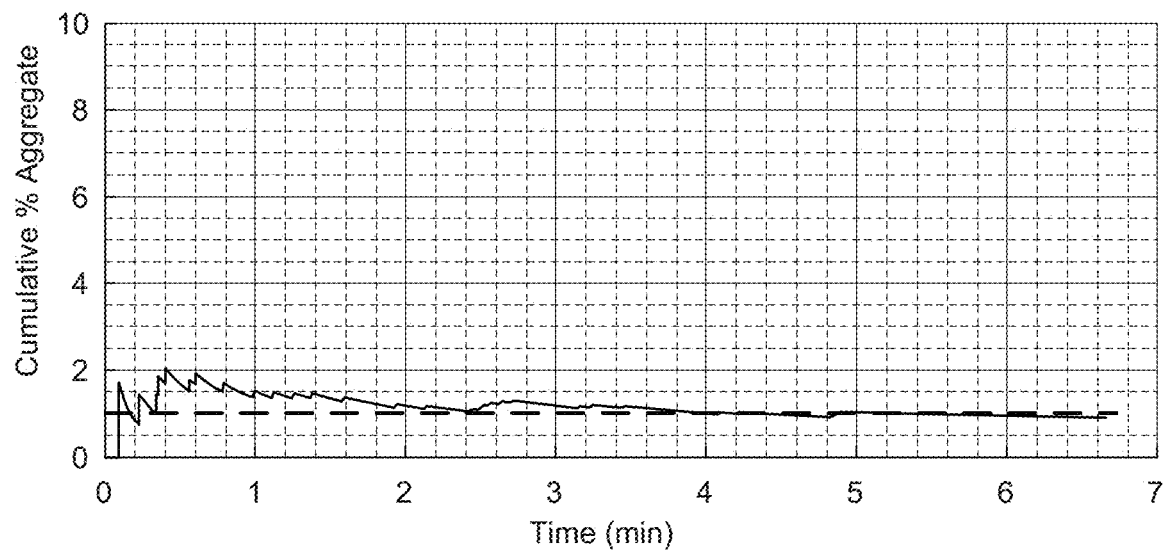
FIG. 21 is a cumulative % aggregation as a function of time for a 1% IgA added to a solution of 1 mg/mL IgG.

To investigate the robustness of the approach, the standard deviation employed was that determined in Example 1. The cumulative % aggregation as a function of time (in a "slow" scanning mode of several minutes) for the 1% IgA in a solution of 1 mg/mL IgG is presented in FIG. 21.

Example 3

Figure 22:
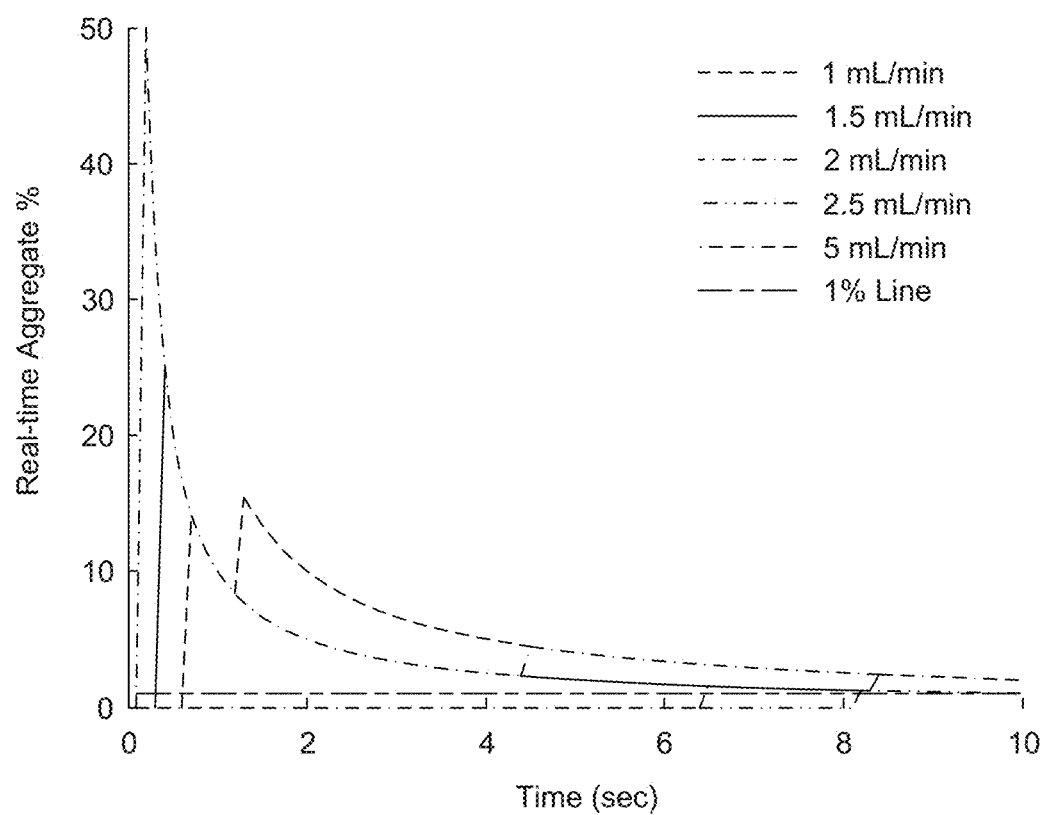
FIG. 22 is a series of real time plots of aggregate % for a 1% IgA in a solution containing 1 mg/mL IgG, detected at different flow rates on a time scale of a few seconds.

An aqueous solution of IgG (1 mg/mL) containing 1% IgA in PBS, prepared as described in Example 2, was used to investigate the feasibility of real time detection, measuring % aggregation over a time scale of a few seconds (e.g., 10 seconds). The known flowrates employed ranged between 1 and 5 mL/minute; the scan volume was 1 microliter; the scan rate was 1 scan per 0.1 seconds. As seen in FIG. 22, the plots for real-time aggregate % for the various flow rates asymptotically approached the known concentration of 1% IgA.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for analyzing for structures in a solution, the method comprising:
    directing light from a light source through the solution, illuminating the solution across a spectral band;
    with a detector, detecting the light from the light source after interaction with the solution and, where the detecting of the light occurs after it interacts with an etalon, separate from the solution; and
    analyzing a response of the detector to resolve contrast information of the etalon to assess the structures in the solution.

2. The method of claim 1, wherein the structures are cells or proteins.

3. The method of claim 1, further comprising splitting the light from the light source to additionally perform absorption spectroscopic analysis of the solution.

4. The method of claim 1, wherein the solution is a flowing solution.

5. The method of claim 1, wherein the solution is in a bioreactor.

6. The method of claim 1, wherein the etalon is established at a volumetric sample detection region of an in-situ probe in a bioreactor.

7. The method of claim 1, wherein the structures form aggregates.

8. The method of claim 1, wherein detecting light from the light source after interaction with the solution and an etalon is conducted in a transmission arrangement.

9. The method of claim 1, wherein detecting light from the light source after interaction with the solution and an etalon is conducted a transflection arrangement.

10. The method of claim 1, further comprising directing the light from the light source to a second etalon before the interaction with the solution.

11. The method of claim 1, wherein the light from the light source is directed first to and trough the solution, then to the etalon.

12. The method of claim 1, wherein the light source is a tunable laser.

13. The method of claim 12, wherein the tunable laser has a linewidth of less than 1 nanometer (nm).

14. The method of claim 12, wherein the tunable laser has a linewidth of less than 0.1 nanometers.

15. The method of claim 1, wherein analyzing the response of the detector includes Fast Fourier Transform processing.

16. The method of claim 15, wherein analyzing the response of the detector further includes converting from a frequency domain to a space domain.

17. The method of claim 1, further comprising obtaining an absorption spectrum of the structures.

18. The method of claim 1, further comprising monitoring changes in contrast information over time.

19. The method of claim 2, wherein the structures are viable cells.

* * * * *